United States Patent
Greiner-Stoeffele et al.

(10) Patent No.: US 10,196,645 B2
(45) Date of Patent: Feb. 5, 2019

(54) EXPRESSION VECTOR

(71) Applicant: C-lecta GmbH, Leipzig (DE)

(72) Inventors: Thomas Greiner-Stoeffele, Leipzig (DE); Meike Hoffmann, Leipzig (DE); Marc Struhalla, Leipzig (DE); Rico Czaja, Leipzig (DE)

(73) Assignee: c-LEcta GmbH, Leipzig (DE)

( * ) Notice: Subject to any disclaimer, the term of this patent is extended or adjusted under 35 U.S.C. 154(b) by 0 days.

(21) Appl. No.: 14/992,723

(22) Filed: Jan. 11, 2016

(65) Prior Publication Data

US 2016/0194647 A1 Jul. 7, 2016

Related U.S. Application Data

(60) Division of application No. 13/162,204, filed on Jun. 16, 2011, now abandoned, which is a continuation of application No. PCT/EP2009/008977, filed on Dec. 15, 2009.

(30) Foreign Application Priority Data

Dec. 16, 2008 (EP) .................................... 08021794

(51) Int. Cl.
C12N 15/70 (2006.01)
C12N 15/63 (2006.01)
C12N 15/10 (2006.01)

(52) U.S. Cl.
CPC ......... *C12N 15/70* (2013.01); *C12N 15/1082* (2013.01); *C12N 15/635* (2013.01); *C12N 2800/40* (2013.01); *C12N 2830/002* (2013.01)

(58) Field of Classification Search
None
See application file for complete search history.

(56) References Cited

U.S. PATENT DOCUMENTS

| | | | |
|---|---|---|---|
| 6,030,807 | A | 2/2000 | De Lencastre et al. |
| 6,689,573 | B1 | 2/2004 | Roberts et al. |
| 6,780,405 | B1 | 8/2004 | Curtiss, III et al. |
| 6,977,165 | B2 | 12/2005 | Farmer |
| 7,005,423 | B1 | 2/2006 | Plaetinck et al. |
| 2002/0132257 | A1 | 9/2002 | Giordano et al. |
| 2005/0266026 | A1 | 12/2005 | Hoffmann et al. |
| 2008/0220518 | A1 | 9/2008 | Greiner-Stoffele et al. |
| 2009/0092578 | A1 | 4/2009 | Su et al. |
| 2012/0288521 | A1 | 11/2012 | Hoffman et al. |

FOREIGN PATENT DOCUMENTS

| | | |
|---|---|---|
| WO | WO 00/01846 A2 | 1/2000 |
| WO | WO 01/83785 A2 | 11/2001 |
| WO | WO 02/083910 A2 | 10/2002 |
| WO | WO 2005/040376 A2 | 5/2005 |

OTHER PUBLICATIONS

Spehr et al., Gene, 257: 259-267, 2000.*
Schmeisser et al. "Metagenomics, Biotechnology with Non-Culturable Microbes", Applied Microbiology and Biotechnology, 2007, pp. 955-962, vol. 75, No. 5 (eight (8) sheets).
Kim et al., "Rare Codon Clusters at 5'-end Influence Heterologous Expression of Archaeal Gene in *Escherichia coli*", Protein Expression and Purification, Nov. 1, 2006, pp. 49-57, vol. 50, No. 1, (nine (9) sheets).
Studier, F. William, "Use of Bacteriophage T7 Lysozyme to Improve an Inducible T7 Expression System", Journal of Molecular Biology, Jan. 1, 1991, pp. 37-44, vol. 219, No. 1, (eight (8) sheets).
International Search Report dated Apr. 26, 2010 (five (5) sheets).
Laemmle, et al., "Identification of novel enzymes with different hydrolytic activities by metagenome expression cloning", Journal of Biotechnology, 2007, pp. 575-592, vol. 127, (Eighteen (18) pages).
Greenfield et al., DNA Sequence of the araBAD promoter in *Escherichia coli* B/r. Proc. Natl. Acad. Sci., USA. Oct. 1978; 75, (10): 4724-8.
Wiggs et al., "Utilization of Promoter and Terminator Sites on Bacteriophage T7 DNA by RNA polymerases from a Variety of Bacterial Orders", Cell., Jan. 16, 1979, (1), pp. 97-109.
Carstens et al., "Methods in Molecular Biology, Use of tRNA-Supplemented Host Strains for Expression of Heterologous Genes in *E. coli*", 25: 2003, pp. 225-233.
Moffat et al., "T7 Lysozyme Inhibits Transcription by T7 RNA polymerase", Cell vol. 49, issue 2, Apr. 24, 1987, pp. 221-227.
Hoffmann et al., "Ambisense" Approach for the Generation of Influenza A Virus: vRNA and mRNA Synthesis from One Template, Virology 267, 310-317 (2000).
Hoffmann et al., A DNA transfection system for generation of influenza A virus from eight plasmids, PNAS 97 (11) 6108-6113 (May 2000).

* cited by examiner

*Primary Examiner* — Nancy Ann Treptow
(74) *Attorney, Agent, or Firm* — Agris & Von Natzmer, LLP; Joyce Von Natzmer

(57) ABSTRACT

An expression vector including two separately inducible converging promoters P1 and P2, and expression system including such an expression vector and an additional regulator vector, a method of protein expression using such an expression system, and a method of investigating (meta) genome libraries using such an expression system.

29 Claims, 6 Drawing Sheets

Specification includes a Sequence Listing.

EXPRESSION VECTOR

CROSS REFERENCE TO RELATED APPLICATIONS

This application is a divisional of U.S. patent application Ser. No. 13/162,204, filed Jun. 16, 2011, which is a continuation of International patent application no. PCT/EP2009/008977, filed Dec. 15, 2009, which claims priority from European patent application no. 08021794.6, filed Dec. 16, 2008, the entire disclosure of which is incorporated herein by reference.

BACKGROUND OF THE INVENTION

The invention relates to an expression vector that is suitable for efficient screening of (meta)genome libraries, preferably in *Escherichia coli*.

Only about 1-5% of all known microorganisms are at present cultivable in the laboratory with current methods. Methods have been developed in recent times which should make it possible to use the genetic resources of non-cultivable microorganisms. This field is also called "metagenomics", with the term "metagenome" denoting the genetic information of all organisms of a particular habitat, regardless of whether these are cultivable or not.

By direct cloning of the DNA obtained from environmental samples into suitable vector systems (plasmids, cosmids, BACs, YACs) this resource becomes available for easy manipulation in the laboratory. These gene banks (metagenome libraries) can be used for example for searching for novel enzymes. Finding completely novel enzyme activities requires activity-based screening of prepared metagenome libraries. A precondition for this is a suitable detection system (agar plate assays, microtitre plate systems), which permits simultaneous screening of the largest possible number of clones (high-throughput screening). Furthermore, expression of the genes must be provided in a heterologous host. In addition to *E. coli*, other organisms such as *Streptomyces lividans* or *Pseudomonas putida* are also employed as host in metagenome studies.

Problems with the metagenome technique relate in particular to expression of the genes found. These include inadequate transcription, for example because promoters are not recognized, toxicity of the products to the host, missing cofactors or chaperones and therefore incorrect folding of the proteins in the heterologous host, and missing secretion systems (W. R. Streit et al., Curr Opin Microbiol. 2004, 7(5), 492-8).

Conventional (meta)genome libraries for screening in *E. coli* are generally constructed in artificial chromosomes (BAC), cosmid or fosmid systems or plasmids. Until now, (meta)genomic plasmid libraries have mainly been constructed using conventional cloning vectors, which generally have an individual, comparatively weak promoter (e.g. lac promoter) or are designed entirely for the use of internal promoters of the cloned DNA. This weak promoter was not originally intended for expression of the cloned DNA, but is present as promoter before the lacZ gene, which is often used as marker. In this connection, reference may be made for example to R. Ranjan et al., Biochem Biophys Res Commun., 2005, 335(1), 57-65; and A. Knietsch et al., Appl Environ Microbiol., 2003, 69(3), 1408-1416.

The relative weakness of the promoter does not have any negative consequences in sequence-based screening of the (meta)genome library. However, if the same plasmid libraries are used for screening the activity of the target proteins encoded by the library, expression of the target proteins is then often based on the weak promoter located at the plasmid. With the cosmid/fosmid systems that are often used, the functional expression of the target genes is based exclusively on recognition and reading of the non-*E. coli* promoters located on the inserted DNA. In this connection, reference may be made for example to K. S. Hong et al., J Microbiol Biotechnol., 2007, 17(10), 1655-60.

Owing to the weakness of the promoter or the non-recognition of non-*E. coli* promoters, some of the target proteins are barely expressed, or not at all, so that activity screening of the target proteins is far more difficult. These limitations make iterative activity screening of sub-libraries (cluster screening, cf. US 2008/220581=WO 2005/040376) impossible in most cases. Instead, complicated and time-consuming activity screening with individual clones, e.g. on agar plates, is necessary.

Another problem in activity screening is that when constructing (meta)genome libraries it is not possible to influence the orientation of the open reading frame (ORF) on the cloned DNA. It is also possible for two successive open reading frames to have different directions of reading. In activity screening with conventional expression vectors, a large part of the sequence information contained in the (meta)genome library is therefore often lost because the promoter used only covers one of the two possible directions of reading.

U.S. Pat. No. 6,780,405 (=WO 01/83785) discloses a regulated system for delivery of antigens. In this system, however, the DNA to be cloned into the insertion sequence is not under the control of both promoters. Instead, one of the two promoters controls the on or a gene for regulating the ori. Such a system is hardly suitable for screening metagenome libraries, as only 50% of the sequence information contained is captured.

U.S. Pat. No. 6,030,807 discloses an operon that codes for enzymes that are linked with the use of L-arabinose. The operon does not, however, have an insertion sequence located between two promoters converging towards each other. The system also does not include a vector with two different promoters converging towards each other, between which an insertion sequence is arranged, in each case downstream.

U.S. Pat. No. 6,977,165 (=WO 02/083910) discloses a method of production of a vector that includes at least one spliceable intron. The vector size is not, however, maximum 3000 bp.

Schmeisser et al., Appl. Microbiol. Biotechnol 2007, 75(5), 955-62 is a review of the subject: Metagenomics, biotechnology with non-cultivable microbes. The publication does not contain any information on expression in plasmids with two promoters converging towards one another, and inducible separately from one another, between which an insertion sequence is arranged, in each case downstream, so that the expression of a DNA sequence cloned into the insertion sequence is placed under the control of both promoters.

U.S. Pat. No. 7,005,423 (=WO 00/01846) discloses a method for identifying DNA that is responsible for a particular phenotype. However, that method does not use a vector with promoters that are inducible separately from one another, and flow towards one another. It is even a precondition of the method that both promoters are identical. The vector does not comprise at most 3000 bp.

S. Kim et al., Prot. Expr Purif. 2006, 50(1), 49-57 discloses rare codon clusters on the 5'-terminus, which have an influence on heterologous expression of archaic genes in

*E. coli.* The publication does not, however, contain any mention of an expression vector that comprises two promoters inducible separately from one another, and converging towards each other, between which an insertion sequence is arranged, in each case downstream, so that the expression of a DNA sequence cloned into the insertion sequence is placed under the control of both promoters.

F. W. Studier, J. Mol. Biol. 1991, 219(1), 37-44 discloses the use of T7 lysozyme bacteriophage for improving an inducible T7 expression system. The system does not, however, have an expression vector that comprises two promoters inducible separately from one another, and converging towards each other, between which an insertion sequence is arranged, in each case downstream, so that the expression of a DNA sequence cloned into the insertion sequence is placed under the control of both promoters.

SUMMARY OF THE INVENTION

An object of the invention is to provide an expression system that is suitable for screening, in particular for activity screening, of (meta)genome libraries and has advantages over the systems of the prior art.

Another object is to provide an expression system that is characterized by a high cloning efficiency linked to efficient, controllable expression.

A further object of the invention is to provide an expression system which captures as large a proportion as possible of the sequence information contained in the (meta)genome library.

These and other objects have been achieved by the invention as described and claimed hereinafter.

A first aspect of the invention relates to an expression vector comprising two promoters $P_1$ and $P_2$, inducible separately from one another, and converging towards each other, wherein preferably an insertion sequence is arranged between $P_1$ and $P_2$, in each case downstream, so that the expression of a DNA sequence cloned into the insertion sequence is placed under the control of $P_1$ and $P_2$; wherein the insertion sequence is a polylinker and/or a sequence that makes integration of DNA sequences by recombination possible; and wherein the expression vector without insertion sequence comprises altogether at most 3000 bp.

In this connection, "under the control of $P_1$ and $P_2$" means that the expression of the cloned, double-stranded DNA sequence can be controlled by $P_1$ and $P_2$. One strand of the cloned, double-stranded DNA sequence is controlled by $P_1$ and the strand of the cloned, double-stranded DNA sequence complementary thereto is controlled by $P_2$. Control is effected preferably in the sense of an operon.

It was found, surprisingly, that the expression vector according to the invention is particularly suitable for activity screening of (meta)genome libraries, as both directions of reading are covered. The loss of half of the sequence information contained in the (meta)genome library or the need to screen double the number of clones, as must be accepted when using conventional expression vectors, can be avoided by the expression vector according to the invention.

Preferably it is an expression vector for *E. coli*, with two strong promoters flanking the multiple cloning site. The promoters are convergent, i.e. their reading directions converge into each other (face-to-face). The promoters inducible independently of one another are preferably a T7 promoter and an ara promoter.

Figure 6:
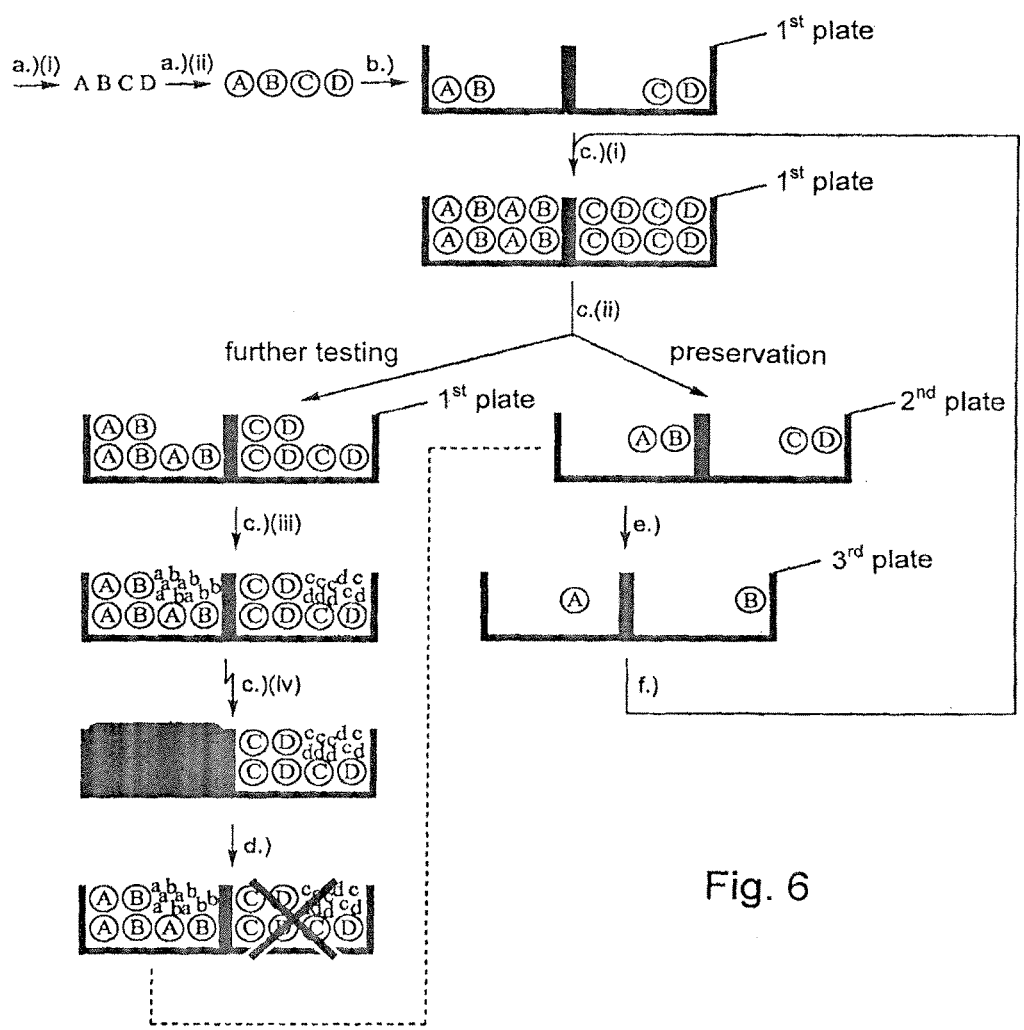
FIG. 6 is an illustration of a preferred embodiment of the method set forth herein.

In a preferred embodiment of such a method, shown schematically in FIG. 6, a library, preferably a (meta) genome library, is prepared (FIG. 6, Step a.)(i)). The library contains the individual variants "A", "B", "C" and "D". According to the invention, this library is transferred into a host (FIG. 6, Step a.) (ii)).

In Step b.) the clones of one partial library are divided into a first compartment (variants "A" and "B" in FIG. 6) and the clones of another partial library into a second compartment (variants "C" and "D" in FIG. 6).

DETAILED DESCRIPTION

An expression vector in the sense of the present invention is preferably a DNA sequence, which comprises at least one DNA sequence for replication in hosts (origin of replication); at least one DNA sequence coding for a sequence that is suitable for distinguishing hosts that contain the expression vector from hosts that do not contain the expression vector (called "selection marker sequence" within the scope of the present invention); at least one DNA sequence for insertion of foreign DNA (called "insertion sequence" within the scope of the present invention), and at least one DNA sequence that is recognized by an RNA polymerase as transcription start point.

The expression vector according to the invention is suitable for the expression of peptides or proteins in prokaryotic or eukaryotic systems (hosts).

Preferred prokaryotic systems comprise e.g. bacteria. Preferred bacteria comprise *E. coli, Bacillus* sp., *Salmonella typhimurium, Staphylococcus* sp., *Pseudomonas* sp., *Streptomyces* sp. and *Caulobacter* sp. and *Borrelia* sp. Preferred eukaryotic systems comprise e.g. yeasts or SF9 cells, Chinese hamster ovary cells, and other cells of higher organisms. Preferred yeasts comprise *Saccharomyces cerevisiae, Schizosaccharomyces pombe* and *Pichia pastoris.*

Various aspects can play a role in selection of the host. An important aspect is the possibility of posttranslational modification of the expressed peptide/protein in the host cell. Another aspect is the suitability of the host cell for secretion of the expressed peptides/proteins. Depending on the biological source of the (meta)genome library, a person skilled in the art can decide which host appears to be the most suitable for expression. The biological source of the (meta) genome library is preferably of purely prokaryotic origin, purely eukaryotic origin or mixed prokaryotic and eukaryotic origin. The source can originate for example from a maritime or terrestrial environment. Possible examples of suitable sources are organisms that live in natural or in artificial, in particular human-influenced, environments. In this connection, comparatively extreme environments may also be considered, e.g. volcanoes, hot springs, deserts, icebound landscapes, glaciers, areas with unusually high or low pH, areas with high radiation exposure or other environmentally exposed biotopes. In a preferred embodiment the sources originate from water treatment works, biofilters or other industrial plant.

Preferably the expression vector according to the invention is a plasmid, e.g. a bacterial plasmid or a yeast plasmid.

In a preferred embodiment the expression vector according to the invention is a low-copy plasmid (on average <100 plasmids per cell). In another preferred embodiment the expression vector according to the invention is a high-copy plasmid (on average ≥100 plasmids per cell).

The origin of replication (ori) used is relevant for the number of copies of the expression vector (not integrated into the chromosome) per cell. A large number of on are known to a person skilled in the art and he is able to select a suitable ori for a particular preferred embodiment. For example, the following ori or ori based on the following ori can be used: $E.$ $coli$ oriC, ColE1-ori or the on from various plasmids known by a person skilled in the art such as pUC, pBR322, pGEM, pTZ, pBluescript, pMB1, pSC101, p15a, pR6K, M13-ori, or, for expression in yeast cells, the 2 μm ori or, for expression in other eukaryotic hosts, ori such as SV40-ori.

According to the invention, the expression vector, in particular the expression plasmid, can also contain several ori, for example 2 ori's. It can, for example, be a combination of a low-copy ori and a temperature-dependent ori or for example ori's that allow propagation in various host organisms (ori for $E.$ $coli$ and ori for $Bacillus$ sp.).

In addition to plasmids, other vectors may also be considered as expression vector according to the invention, for example phage, cosmids, phasmids, fosmids, bacterial artificial chromosomes, yeast artificial chromosomes, viruses and retroviruses (for example vaccinia, adenovirus, adeno-associated virus, lentivirus, herpes-simplex virus, Epstein-Barr virus, fowlpox virus, pseudorabies, baculovirus) and vectors derived therefrom.

The expression vector or parts thereof can also be integrated into the genome.

Any other vector can also be used for production of the expression vector according to the invention, provided it is replicable and capable of surviving in the selected system (host).

Depending on the (meta)genome library and the host that appears suitable for expression, selection of the promoters $P_1$ and $P_2$ preferably takes place on a suitable vector.

According to the invention, the term "promoter" comprises any transcription control sequence that makes it possible to express a peptide or protein in a suitable system, i.e. to transcribe the encoded DNA sequence into RNA and then translate it into the corresponding peptide or protein sequence. Therefore the term comprises not only the promoter sequence as such (the binding site of the RNA polymerase), but optionally, in addition also the enhancer sequence, the operator sequence, and the like.

All nucleotide sequences in the DNA of the expression vector basically come into consideration according to the invention as promoters $P_1$ and $P_2$, to which RNA polymerases bind, to start transcription. It is preferably RNA polymerase of native, naturally occurring organisms, e.g. $E.$ $coli$. The term also comprises, with respect to a given host, promoters on which RNA polymerases of other organisms bind. For example, the RNA polymerase of the T7-bacteriophage can be co-expressed in $E.$ $coli$, so as to be able to use the T7 promoter in $E.$ $coli$, e.g. in $E.$ $coli$ BL21(DE3).

Within the scope of the present invention, "$P_i$" designates optionally $P_1$ or $P_2$.

In a preferred embodiment, $P_1$ and $P_2$ are prokaryotic promoters. In another preferred embodiment, $P_1$ and $P_2$ are eukaryotic promoters.

In a preferred embodiment, $P_1$ and $P_2$ can in each case both be addressed by the same organism, i.e. they can perform their functionality in the same organism and are compatible with the same organism. If, for example, the expression vector according to the invention is in a particular microorganism, preferably both promoters $P_1$ and $P_2$ can be recognized by the RNA polymerases contained in this microorganism; preferably no further organisms are required for this.

Prokaryotic promoters usually comprise a so-called "−35 element" and the so-called "TATA box" or "Pribnow box". The consensus sequence for the −35 element comprises the following six nucleotides: TTGACA. The consensus sequence for the Pribnow box comprises the six nucleotides TATAAT. In a preferred embodiment the two promoters $P_1$ and $P_2$ differ in at least 1 nucleotide within the whole of these two sequence segments, preferably in at least 2 nucleotides, more preferably at least 3 nucleotides, most preferably at least 4 nucleotides and in particular at least 5 nucleotides. In another preferred embodiment the two promoters $P_1$ and $P_2$ differ in at most 5 nucleotides within the whole of these two sequence segments, preferably at most 4 nucleotides, more preferably at most 3 nucleotides, and most preferably at most 2 nucleotides and in particular at most 1 nucleotide.

In a preferred embodiment promoter $P_1$ differs in at least 1 nucleotide, preferably in at least 2 nucleotides, more preferably at least 3 nucleotides, and most preferably at least 4 nucleotides and in particular at least 5 nucleotides from the totality of the two aforementioned consensus sequences. In another preferred embodiment promoter $P_1$ differs in at most 5 nucleotides, preferably at most 4 nucleotides, more preferably at most 3 nucleotides, and most preferably at most 2 nucleotides and in particular at most 1 nucleotide from the totality of the two aforementioned consensus sequences.

In a preferred embodiment, moreover, promoter $P_2$ differs in at least 1 nucleotide, preferably in at least 2 nucleotides, more preferably at least 3 nucleotides, and most preferably at least 4 nucleotides and in particular at least 5 nucleotides from the totality of the two aforementioned consensus sequences. In another preferred embodiment, moreover, promoter $P_2$ differs in at most 5 nucleotides, preferably at most 4 nucleotides, more preferably at most 3 nucleotides, and most preferably at most 2 nucleotides and in particular at most 1 nucleotide from the totality of the two aforementioned consensus sequences.

The distance between the TATA box and the "−35 box" also has an influence on the strength of the promoter. Preferably the distance between the TATA box and the "−35 box" of promoter $P_1$ is 5 to 50 bp, preferably 10 to 30 bp, more preferably 12 to 25 bp, more preferably 15 to 20 bp, and most preferably 17 bp. Preferably the distance between the TATA box and the "−35 box" of promoter $P_2$ is 5 to 50 bp, preferably 10 to 30 bp, more preferably 12 to 25 bp, more preferably 15 to 20 bp, and most preferably 17 bp.

Preferably $P_1$ and $P_2$ are externally regulated, i.e. they are functional promoters, whose activity can be altered (increased or decreased) by at least one other element (molecule, component, cofactor, transcription factor, etc.).

Suitable promoters and their partial sequences are known by a person skilled in the art. Examples of suitable promoters comprise viral, vegetable, bacterial, fungal, human and animal promoters, e.g. cos-, tac-, trp-, tet-, trp-tet-, lpp-, lac-, lpp-lac-, laclq-, T7-, T5-, T3-, gal-, trc-, ara-, SP6-, I-PR- or in the I-PL-promoters or partial sequences thereof, which preferably find application in Gram-negative bacteria. Further advantageous promoters are contained for example in the Gram-positive promoters such as amy, npr, apr and SP02, in the yeast promoters such as ADC1, MFa, AC, P-60, CYC1, GAPDH or in mammalian promoters such as CaM-kinase II, CMV, Nestin, L7, BDNF, NF, SV40, RSV, HSV-TK, metallothionein gene, MBP, NSE, beta-globin, GFAP, GAP43, tyrosine hydroxylase, kainate receptor subunit 1, glutamate receptor subunit B. In principle all natural promoters such as those mentioned above can be used. Furthermore, synthetic promoters can also be used advantageously.

Preferably, $P_1 \ne P_2$.

In one preferred embodiment, one of the two promoters $P_1$ and $P_2$ is intrinsic with respect to the host used, i.e. at least one intrinsic RNA polymerase of the host is able to bind to the promoter and catalyse a transcription, and the other promoter is extrinsic with respect to the host used, i.e. no intrinsic RNA polymerase of the host is able to bind to the promoter and catalyse a transcription. In this connection, extrinsic means that the wild type of the host does not code for this RNA polymerase. In this connection, "catalyse transcription" means that the intrinsic RNA polymerases of the host achieve, in a corresponding in-vitro transcription assay, at most 10%, preferably at most 1%, more preferably at most 0.1% of the transcription rate as the extrinsic RNA polymerase present for this promoter. In this embodiment, the correspondingly required extrinsic RNA polymerase is coexpressed.

In another preferred embodiment, gene expression by $P_1$ is regulated by an individual specific factor, namely by the regulator $R_1$. In another preferred embodiment, gene expression by $P_1$ is regulated by at least two specific factors, namely by the regulators $R_1^a$ and $R_1^b$, wherein $R_1^a$ can for example be a repressor and $R_1^b$ can for example be an activator. This applies analogously to $P_2$ and $R_2$ or $R_2^a$ and $R_2^b$.

In a preferred embodiment (a) the promoter $P_1$ and/or the promoter $P_2$ requires that, for binding of the RNA polymerase to the corresponding recognition sequence of the promoter, a regulator $R_1$ or $R_2$ is bound to the promoter, i.e. transcription takes place provided there is binding of $R_1$ to $P_1$ or of $R_2$ to $P_2$.

In another preferred embodiment (b) the promoter $P_1$ and/or the promoter $P_2$ requires that, for binding of the RNA polymerase to the corresponding recognition sequence of the promoter, a regulator $R_1$ or $R_2$ is not bound to the promoter, i.e. transcription takes place provided there is no binding of $R_1$ to $P_1$ or of $R_2$ to $P_2$. An example of such interaction of promoter and regulator is the interaction of a T7 promoter extended by at least one lacO operator sequence in combination with the repressor LacI.

In another embodiment (c) the promoter $P_1$ and/or the promoter $P_2$ requires that, for binding of the RNA polymerase to the corresponding recognition sequence of the promoter, a regulator $R_1$ or $R_2$ is bound to the promoter, but the regulator $R_1$ or $R_2$ can assume various conformations, without thereby permanently removing the binding to the promoter, and transcription then only takes place provided $R_1$ or $R_2$ is in one of the possible conformations. An example of said interaction of promoter and regulator is the interaction of the ara promoter with its activator/repressor AraC.

Preferably the promoters $P_1$ and $P_2$ belong to different of these embodiments (a), (b) and (c), especially preferably (a) and (c).

Preferably the system $P_1/R_1$ and/or the system $P_2/R_2$ is influenced by another element $I_1/I_2$ (inductors) or a change of the external conditions. These inductors $I_1$ or $I_2$ can for example be biomolecules, which are synthesized by the host, or natural or artificial molecules, which are added from outside. In particular a temperature change may also be considered as a change of the external conditions.

Especially preferably $I_1$ is an inductor for $P_1$, but not for $P_2$, and/or $I_2$ is an inductor for $P_2$, but not for $P_1$.

In a preferred embodiment promoter $P_1$ and/or promoter $P_2$ comprises, in addition to the binding site for the RNA polymerase, at least one enhancer sequence located outside of this binding site and/or at least one operator sequence.

Enhancers are typically localized in the 3'-untranslated region of the sequence to be expressed. These enhancer sequences can be of prokaryotic or eukaryotic origin. They can be variants of these sequences or can be synthetic enhancer sequences.

In one embodiment the enhancer sequence is the wild-type enhancer sequence of the selected promoter.

Preferably $P_1$ and $P_2$ comprise in each case independently of one another at most 1000 bp, preferably at most 900 bp and especially preferably at most 800 bp. The presence/embodiment of the Shine-Dalgarno sequence also has an influence on the expression rate in prokaryotic hosts. The consensus sequence of the Shine-Dalgarno sequence in *E. coli* is AGGAGG. In a preferred embodiment, in connection with promoter $P_1$, a Shine-Dalgarno sequence is used that coincides in at least 4 nucleotides, preferably at least 5 nucleotides, more preferably 6 nucleotides, and most preferably completely with the consensus sequence.

In a preferred embodiment, in connection with promoter $P_2$, a Shine-Dalgarno sequence is used that coincides in at least 4 nucleotides, preferably at least 5 nucleotides, more preferably 6 nucleotides, and most preferably completely with the consensus sequence.

The Kozak sequence has a similar influence on the expression rate in eukaryotic hosts. The Kozak sequence for mammals for example has the consensus sequence (GCC) GCCR-CCAUGG (<SEQ. ID. NO: 3>), wherein R is a purine, which is located 3 bp upstream of the start codon AUG and wherein a guanine is located downstream of the start codon and the Kozak sequence of yeasts has for example the consensus sequence (A/U)A(A/C)AA(A/C) AUGUC(U/C) (<SEQ. ID. NO: 4>).

In one preferred embodiment the consensus sequence is used in connection with promoter $P_1$ in a eukaryotic host.

In another preferred embodiment the consensus sequence is used in connection with promoter $P_2$ in a eukaryotic host.

In yet another preferred embodiment, on the empty expression vector according to the invention, neither a Shine-Dalgarno sequence nor a Kozak sequence is arranged on the insertion sequence in both reading directions. This preferred embodiment relates to the expression vector in the original state, i.e. in the state in which no DNA to be expressed or other DNA has been cloned into the insertion sequence (e.g. the polylinker). Such a vector is also known as "empty vector" by a person skilled in the art. In this embodiment of the expression vector according to the invention, the sequence to be cloned into the insertion sequence then preferably comprises a Shine-Dalgarno sequence or a Kozak sequence.

The in vivo promoter strength is defined by the RNA synthesis rate that is triggered by a single promoter sequence, and leads to a corresponding proportion of the desired target protein in the total protein content of the host organism. The promoters used lead to a content of an expressed target protein relative to the total protein content of preferably >1%, preferably >5%, more preferably >10%, and most preferably >25%, in particular >50%.

The two promoters $P_1$ and $P_2$ converge together according to the invention, i.e. they are convergent, face-to-face. Convergent promoters are produced by arranging promoter $P_1$ on one DNA strand and promoter $P_2$ on the complementary DNA strand of the expression vector. In other words, according to the invention, promoter $P_1$ and the sequence complementary to promoter $P_2$ are arranged on one DNA strand and promoter $P_2$ and the sequence complementary to promoter $P_1$ are arranged on the complementary DNA strand of the expression vector.

Convergent promoters are to be distinguished from bidirectional promoters, even though the two terms are occasionally used synonymously in the literature.

In its true sense, a bidirectional promoter denotes a promoter region or two back-to-back cloned promoters, whose reading directions point away from each other, and with which two open reading frames flanking the promoter region are read. Such promoters are widely distributed, as they can be used in the coexpression of a reporter gene present in stoichiometric ratio to the target gene, in particular in cell cultures. In this connection, reference may be made for example to Sammarco et al., Anal. Biochem. 2005, 346(2), 210-216; Baron et al. Nucleic Acids Res. 1995, 23(17), 3605-6; and EP-A 1 616 012.

In contrast, convergent promoters, such as the promoters $P_1$ and $P_2$ according to the invention, are two face-to-face cloned promoters, whose reading directions point toward each other. Owing to the circular structure of plasmids and other expression vectors in circular form, bidirectional promoters can also be oriented face-to-face in some way, although not relative to the insertion sequence, which according to the invention is preferably arranged between the two promoters $P_1$ and $P_2$ in each case downstream, so that the two promoters $P_1$ and $P_2$ flank the insertion sequence on both sides. In this way, by means of the promoters it is possible to control the expression of DNA sequences, which have previously been cloned into the region of the insertion sequence, and namely in both directions of reading.

According to the invention, therefore preferably an insertion sequence is arranged between $P_1$ and $P_2$, in each case downstream, so that the expression of a DNA sequence cloned into the insertion sequence is placed under the control of $P_1$ and $P_2$. In other words $P_1$ and $P_2$ run both towards each other, and towards the insertion sequence.

Such insertion sequences are known by a person skilled in the art. Preferably said insertion sequence is a polylinker.

For the purpose of this description, a polylinker (also known by a person skilled in the art as multiple cloning site (MCS)) means a DNA segment in a vector, whose sequence contains various cleavage sites for restriction endonucleases following closely one after another. This makes flexible cloning possible, as the one that is most suitable in each case can be selected and used from the various restriction cleavage sites. The cleavage sites are in this case unique on the vector.

In one preferred embodiment, the polylinker comprises at least 1, preferably at least 2 or at least 3, more preferably at least 4 or at least 5, and most preferably at least 6 or at least 7 and in particular at least 8 or at least 9 recognition sequences for restriction endonucleases, which optionally overlap. In this connection, the restriction endonucleases are preferably restriction endonucleases of type I, II or III, which are listed in the REBASE database (http://rebase.neb.com/rebase). Furthermore, in this connection, recognition sequences for restriction endonucleases are to be understood preferably as penta-, hexa-, hepta- or octamers preferably of a double-stranded DNA sequence. Preferably the hexa- or octamers are palindromic, i.e. on both strands in one direction (for example 5'-3') they show the same base sequence, e.g. GAATTC or GCGGCCGC. In another preferred embodiment these recognition sequences are interrupted, i.e. between parts of the fixed recognition sequences there are freely selectable sequences, e.g. CACNNNNGTG (SEQ ID No. 5) or GCNNGC.

In yet another preferred embodiment the polylinker comprises a sequence segment of at most 20 bp, preferably of at most 15 bp, on which there are at least 1 or at least 2, preferably at least 3 or at least 4, more preferably at least 5 or at least 6, and most preferably at least 7 or at least 8, and in particular at least 9 or at least 10 cleavage sites of restriction endonucleases, which optionally can overlap. In this connection, restriction endonucleases are preferably to be understood as restriction endonucleases of type I, II or III, which are listed in the REBASE database (http://rebase.neb.com/rebase).

In addition to restriction endonucleases, basically homing endonucleases can also be considered.

In one preferred embodiment, between the last by of promoter $P_1$ and the last by of promoter $P_2$, an insertion sequence is arranged in face-to-face arrangement, which comprises at most 500 bp, preferably at most 200 bp, more preferably at most 100 bp, more preferably at most 50 bp, and most preferably at most 20 bp and in particular at most 6 bp. In this connection the expression "last bp" refers to the reading direction of the RNA polymerase. This preferred embodiment relates to the expression vector in the original state, i.e. in that state in which no DNA to be expressed or other DNA has yet been cloned into the insertion sequence (e.g. the polylinker) (empty vector).

In an especially preferred embodiment, on the insertion sequence there are at most 100, preferably at most 50, preferably at most 20, preferably at most 10 cleavage sites, preferably at most 5 cleavage sites and especially preferably at most 1 cleavage site of restriction endonucleases, which preferably have a recognition sequence between 4 and 10 b and produce overhanging or smooth ends. Especially preferably, the restriction endonucleases are selected from the group comprising AanI (PsiI), AarI, AasI (DrdI), AatII, Acc65I (KpnI), AdeI (DraIII), AjiI (BmGBI), AjuI, AlfI, AloI, AluI, Alw21I (BsiHKAI), Alw26I (BsmAI), Alw44I (ApaLI), ApaI, BamHI, BauI (BssSI), BclI, BcnI (NciI), BcuI (SpeI), BdaI, BfiI (BmrI), BfmI (SfcI), BfuI (BciVI), BglI, BglII, Bme1390I ScrFI), BoxI (PshAI), BpiI (BbsI), BplI, Bpu10I, Bpu1102I (BlpI), BseDI (BsaJI), BseGI (FokI), BseJI (BsaBI), BseLI (BslI), BseMI (BsrDI), BseMII (BspCNI), BseNI (BsrI), BseSI Bme1580I), BseXI (BbvI), Bsh1236I (BstUI), Bsh1285I (BsiEI), BshNI (BanI), BshTI (AgeI), Bsp68I (NruI), Bsp119I (BstBI), Bsp120I (PspOMI), Bsp143I (Sau3AI), Bsp1407I (BsrGI), BspLI (NlaIV), BspOI (BmtI), BspPI (AlwI), BspTI (AflII), BsT1107I (BstZ17I), BstXI, Bsu15I ClaI), BsuRI (HaeIII), BveI (BspMI), CaiI (AlwNI), CfrI (EaeI), Cfr9I (XmaI), Cfr10I (BsrFI), Cfr13I (Sau96I), Cfr42I (SacII), CpoI (RsrII), CseI (HgaI), Csp6I (CviQI), DpnI, DraI, Eam1104I (EarI), Eam1105I (AhdI), Eci136II (EcoICRI), Eco24I (BanII), Eco31I (BsaI), Eco32I (EcoRV), Eco47I (AvaII), Eco47III (AfeI), Eco52I (EagI), Eco57I (AcuI), Eco57MI, Eco72I (PmlI), Eco81I (Bsu36I), Eco88I (AvaI), Eco91I (BstEII), Eco105I (SnaBI), Eco130I (StyI), Eco147I (StuI), EcoO109I (DraII), EcoRI, EcoRII, EheI (NarI), Esp3I (BsmBI), FaqI (BsmFI), FspAI, FspBI (Bfai), GsuI (BpmI), HhaI, Hin1I (AcyI), Hin1II (NlaIII), Hin4I, Hin6I (HinP1I), HincII (HindII), HindIII, HinfI, HpaII, HphI, Hpy8I (MjaIV), HpyF3I (DdeI), HpyF10VI (MwoI), KpnI, Kpn2I (BspEI), KspAI (HpaI), LguI (SapI), Lsp1109I (BbvI), LweI (SfaNI), MauBI MbiI (BsrBI), MboI, MboII, MlsI (MscI), MluI, MnlI, Mph1103I (NsiI), MreI (Sse232I), MspI (HpaII), MssI (PmeI), MunI (MfeI), MvaI (BstNI), Mva1269I (BsmI), NcoI, NdeI, NheI, NmuCI (Tsp45I), NotI, NsbI (FspI), OliI (AleI), PaeI (SphI), PagI (BspHI), PasI, PauI (BssHII), PdiI (NaeI), PdmI (XmnI), PfeI (TfiI), Pfl23II (BsiWI), PfoI, PpiI, Ppu21I (BsaAI), PscI (PciI), Psp5II (PpuMI), Psp1406I (AclI), PstI, PsuI (BstYI), PsyI (Tth111I), PvuI, PvuII, RsaI, RsaI (MsII), SacI, SalI, SatI (Fnu4HI), ScaI, SI (PleI), SdaI (SbfI), SduI (Bsp1286I), SfaAI (AsISI), SphiI, SgrDI, SgsI (AscI), SmaI, SmiI (SwaI), SmoI (SmlI), SmuI (FauI), SsiI (AcyI), SspI, TaaI (HpyCH4III), TaiI (MaeII), TaqI, TasI (Tsp509I), TatI, TauI, Tru1I (MseI), TscAI (TspRI), TsoI, TstI, Van91I (PflMI), VspI (AseI), XagI (EcoNI), XapI (ApoI), XbaI, XceI (NspI), XhoI, XmaJI (AvrII) and XmiI (AccI).

Especially preferably the insertion sequence comprises at most 50 bp and has at least 6 cleavage sites for restriction endonucleases.

To ensure a translation in all three reading frames, in a preferred embodiment according to the invention a system of expression vectors is also comprised, in which the whole sequence or parts of the sequence of the polylinker are in each case displaced by one nucleotide with respect to the rest of the vector sequence. For illustration of this teaching, reference should be made to the works of Charnay et al. (1978) Nucl. Acid Res. 5: 4479 and Villa-Komaroff (1978) Proc. Natl. Acad. Sci. 75, 3727.

In another preferred embodiment the empty expression vector according to the invention does not comprise a translation start, i.e. there is also no start codon ATG or GTG within the insertion sequence in both directions of reading. In this preferred embodiment, the sequence to be cloned into the insertion sequence then preferably contains said translation start including a start codon.

In one preferred embodiment, there is no ribosome binding site on the insertion sequence in both directions of reading. It is thereby ensured that translation of the resultant mRNA cannot be initiated by the empty vector of the two promoters. Especially preferably the empty expression vector according to the invention contains neither ribosome binding sites nor start codons in the insertion sequence in both directions of reading.

In an especially preferred embodiment, on the insertion sequence there is (still) no gene, e.g. for a particular antibiotic resistance, so that the empty expression vector only contains the insertion sequence as such between $P_1$ and $P_2$. In this way it is ensured that both promoters relate functionally to the insertion sequence, i.e. to both DNA strands of the insertion sequence, so that cloning into the insertion sequence can take place undirected. In this connection, "undirected" means that according to the invention, ultimately it does not matter into which of the two DNA strands of the plasmid a particular sequence is inserted, as both promoters relate functionally to the insertion sequence, the inserted sequence is inevitably placed either under the control of $P_1$ or under the control of $P_2$. Expression of the inserted sequence is thus ensured in each case.

Conversely, if in the empty expression vector a gene were already to be placed under the control of e.g. $P_1$, for example a gene for a particular antibiotic resistance, undirected cloning would not be possible (or at least would be associated with disadvantages), as a (further) insertion downstream of $P_1$ would always result in coupling of expression of the inserted sequence with the gene already present. For the case when the gene for antibiotic resistance is followed by a terminator, the inserted foreign DNA, which would be inserted after the gene, would only be under the control of the relevant promoter to a limited extent, or not at all, and the advantage according to the invention, of two promoters directed on the same insertion sequence, would be lost.

Decoupling of expression of the inserted sequence from the gene that is under the control of $P_1$ would however necessitate a directed cloning into the insertion sequence downstream of $P_2$, i.e. specifically into the other DNA strand. However, directed clonings require a corresponding 5'-3'-orientation of the sequence to be inserted, so that by means of such an expression vector ultimately it would still only be possible to screen 50% of a DNA variant library.

In an alternative embodiment, the expression vector according to the invention can contain as insertion sequence, instead of or additionally to a polylinker, also a sequence that permits integration of DNA sequences by recombination.

Methods for integrating DNA sequences into a vector, preferably an expression vector, are known by a person skilled in the art. For example, such a method is based on recombination via att-sites, as for example in the GATEWAY vectors of the company Invitrogen (Carlsbad, Calif., USA). Another method is described in Muyrers J. P. P., Zhang Y., and Stewart A. F. (2001) "Recombinogenic engineering—new options for cloning and manipulating DNA" TIBS 26: 325-331. The DNA to be cloned a (meta-)genome bank would then have to be pretreated with corresponding linkers. Methods for attaching linkers to DNA are known by persons skilled in the art.

In one preferred embodiment, a secretion sequence that has the purpose that, after expression, the host secretes the expressed peptide or protein, is arranged after the last by of $P_1$ and/or after the last by of $P_2$, but before the polylinker. For this, it is necessary that there is no stop codon between the secretion sequence and the polylinker. Then the cloned DNA sequences are preferably searched for sequences that produce, as a result of cloning, a fusion protein of signal peptide and encoded protein. Suitable secretion sequences are biologically defined and are known by a person skilled in the art.

In another preferred embodiment, in addition to the polylinker and/or DNA sequences for recombination, the insertion sequence also comprises a so-called suicide sequence. Suicide sequences are sequences that lead to dying-off of certain hosts. For example, the suicide sequence codes for a restriction endonuclease (e.g. EcoRI), which through digestion of the genomic DNA leads to dying-off of hosts that do not encode an associated methyltransferase (e.g. EcoMI) which protects the own DNA. The cleavage sites of the polylinker are in this case arranged within the suicide sequence. If additional DNA sequences are now cloned into the polylinker, the suicide gene is interrupted and becomes inactive. This prevents the formation of so-called religands, i.e. vectors that are religated again without additional DNA, during cloning of the DNA and subsequent transformation of the vectors into suitable hosts. In this case, the expression vector according to the invention is preferably produced in a host that expresses the corresponding protective methyltransferase, whereas the banks are then constructed in a host that does not encode the protective methyltransferase. A great variety of other suicide systems are known by a person skilled in the art. For example, reference may be made to the pJET system from the company Fermentas (Vilnius, Lithuania); Quandt J and Hynes M F (1993) "Versatile suicide vectors which allow direct selection for gene replacement in gram-negative bacteria", Gene 127, 15-21; Ortiz-Martin et al., (2006) "Suicide vectors for antibiotic marker exchange and rapid generation of multiple knockout mutants by allelic exchange in Gram-negative bacteria", J Microbiol Methods. 67, 395-407; Schlieper et al., (1998) "A Positive Selection Vector for Cloning of Long Polymerase Chain Reaction Fragments Based on a Lethal Mutant of the crp Gene of *Escherichia coli*", Anal. Biochem. 257, 203-209 or Bej et al., (1988) "Model suicide vector for containment of genetically engineered microorganisms.", Appl Environ Microbiol. 54, 2472-7.

Convergent promoters are known from the prior art. Thus, in some commercial cloning plasmids there are two convergent promoters on either side of the polylinker (multiple cloning site, MCS), e.g. T7 and SP6 promoter in pDrive (Merck, Darmstadt). However, these cloning plasmids are not expression plasmids, as they do not serve for functional expression of the cloned genes in vivo, but only for generating RNA by in-vitro transcription, e.g. for Northern blots, and as primer sites that are often used for sequencing. Moreover, the convergent promoters are not independently inducible on these cloning vectors. Convergent promoters are also described for plasmids, with which sense and antisense RNA is said to be produced simultaneously, to obtain siRNA and dsRNA for gene silencing in eukaryotes (cf. e.g. Waterhouse et al., Plant Biology, 1998, 95, 13959-64; Zheng et al., PNAS, 2004, 101, 135-40. Convergent promoters also occur naturally in bacteria, e.g. in *Bacillus*, where two promoters effect the reading of two different gene products on the sense and antisense strand of the same DNA segment (Wang et al., J. Bacteriol., 1999, 181, 353-6).

The use of a vector with two convergent promoters for screening a (meta)genome library is also described in the literature (cf. Lammle et al., Journal of Biotechnology, 2007, 127, 575-92). This is the vector pJOE930 (Altenbuchner et al., Methods Enzymol., 1992, 216, 457-66), which bears two convergent, comparatively weak lac promoters and can be used for the cloning and IPTG-induced expression of metagenomic DNA. The palindromic sequence of the two lac promoters and the MCS enclosed by them cause instability of the empty vector in *E. coli*. Furthermore, owing to their similarity, the two promoters are not separately inducible.

It was found, surprisingly, that separately inducible convergent promoters have advantages over convergent promoters that are not separately inducible.

For the purpose of this description, separate inducibility of the promoters $P_1$ and $P_2$ means that promoter $P_1$ can be induced selectively by suitable measures, without promoter $P_2$ also being induced simultaneously to a significant extent, and vice versa. Preferably, in selective induction of promoter $P_1$, promoter $P_2$ is induced by at most 10% of its maximum inducibility, preferably at most 1%, more preferably at most 0.5%, and most preferably at most 0.2% and in particular at most 0.1%, and vice versa. Separate inducibility of the promoters can be achieved in the simplest case by using promoters $P_1$ and $P_2$ that interact with different modulators (repressors, activators).

The empty expression vector according to the invention has, without the insertion sequence, altogether at most 3000 bp, i.e. the complete sequence of the expression vector including $P_1$ and $P_2$ but excluding the insertion sequence comprises at most 3000 bp.

In a preferred embodiment, the empty expression vector according to the invention comprises, after opening in the insertion sequence or after cutting out parts of the insertion sequence that are not required, altogether at most 3000 bp, preferably at most 2900 bp, preferably at most 2800 bp, preferably at most 2700 bp, more preferably at most 2600 bp, and most preferably at most 2550 bp and in particular at most 2500 bp.

In another preferred embodiment the empty expression vector according to the invention as such comprises altogether at most 3000 bp, preferably at most 2900 bp, preferably at most 2800 bp, preferably at most 2700 bp, more preferably at most 2600 bp, and most preferably at most 2550 bp and in particular at most 2500 bp.

In yet another preferred embodiment the empty expression vector according to the invention, without insertion sequence, comprises altogether at most 2900 bp, preferably at most 2800 bp, preferably at most 2700 bp, more preferably at most 2600 bp, and most preferably at most 2550 bp and in particular at most 2500 bp.

Preferably the expression vector according to the invention does not code for a regulator of $P_1$ and/or a regulator of $P_2$.

In a preferred embodiment of the expression vector according to the invention, $P_1$ is a T7 promoter. The T7 promoter is known by a person skilled in the art. In this connection, for example reference may be made in its entirety to Studier and Moffatt (1986) "Use of bacteriophage T7 RNA polymerase to direct selective high-level expression of cloned genes" J Mol Biol 189, 113-130. The term "T7 promoter" denotes, in the sense of the present invention, a promoter that is recognized as transcription start by the T7-RNA polymerase and that has been expanded by at least one lacO operator sequence. LacI is then the repressor of the T7 promoter.

In a preferred embodiment of the expression vector according to the invention, $P_2$ is a promoter that is regulated by arabinose ($I_2$), in particular the ara promoter. In a preferred embodiment it is an ara promoter from Gram-negative bacteria, preferably *E. coli*. In this case the expression vector according to the invention preferably does not code for the regulator AraC of the ara promoter.

The ara promoter is known by a person skilled in the art. The arabinose operon consists of a controllable promoter region (ara promoter), and three structural genes (araB, araA and araD), which code for proteins for degradation of L-arabinose. AraC is expressed constitutively. The gene product serves as a repressor. It binds to the promoter and thus prevents transcription of the genes araB, araA and araD. If arabinose is present, it binds to AraC. As a result of arabinose being bound, AraC changes its shape, binds to other DNA sequences and thus becomes the activator. Therefore the RNA polymerase can now attach to the promoter, and transcription of the structural genes begins. When the arabinose has degraded completely, AraC changes conformation again and transcription stops again. For further details, reference may be made for example to Schleif R. (2000) Regulation of the L-arabinose operon of *Escherichia coli*. Trends Genet. 16, 559-65 in its entirety.

In another preferred embodiment the expression vector according to the invention is characterized in that it codes in each case for at least one terminator $T_1$ or $T_2$ in the corresponding direction of reading of the promoters $P_1$ or $P_2$.

In a preferred embodiment of this, the expression vector has the following arrangement of $P_1$, $P_2$, $T_1$, $T_2$ and of the insertion sequence: $T_2$ (antisense)-$P_1$ (sense)-insertion sequence (sense/antisense)-$P_2$ (antisense)-$T_1$ (sense).

Especially preferably, $T_1$ is a T7-terminator. Especially preferably, $T_2$ is a terminator for the host RNA polymerase.

In a preferred embodiment the terminator for the T7 promoter is the T7-terminator and the terminator for the ara promoter is a terminator sequence for the *E. coli* RNA polymerase. In an especially preferred embodiment no independent terminator is cloned for the ara promoter, instead the terminator of the gene of the expression vector located upstream cloned in antisense is used.

Within the scope of the present invention, "$T_i$" denotes optionally $T_1$ or $T_2$.

In another especially preferred embodiment the expression vector is characterized in that an additional gene is located between $P_i$ and its terminator $T_i$ in the direction of reading of $P_i$ but after the second promoter $P_j$.

Furthermore, the expression vector according to the invention comprises a selection marker sequence, which is suitable for distinguishing hosts that contain the expression vector, from hosts that do not contain the expression vector.

This can for example be achieved by the selection marker sequence endowing the host with antibiotic resistance, so that it is capable of surviving on nutrient media on which other hosts, which do not contain the expression vector, die. Suitable sequences that impart antibiotic resistance are known by a person skilled in the art. The antibiotic against which resistance is imparted by the selection marker sequence is preferably selected from the group comprising ampicillin, tetracycline, kanamycin, chloramphenicol, spectinomycin, hygromycin, sulphonamide, trimethoprim, bleomycin/phleomycin, Zeocin™, gentamicin and blasticidin.

Alternatively, auxotrophic hosts (negative mutants) can be used, which are dependent on a particular nutrient for survival (amino acid, carbohydrate, etc.), which they cannot synthesize themselves. These hosts are then not capable of surviving on a nutrient medium that does not supply this nutrient. In this case the selection marker sequence on the expression vector according to the invention endows the host with the ability to synthesize this nutrient, so that capability of surviving on the deficient nutrient medium is induced by the expression vector. Suitable selection marker sequences are known by a person skilled in the art.

In the case of yeast cells, the markers used can be those that enable auxotrophic yeast strains to grow without additional uracil, tryptophan, histidine, leucine or lysine in the medium.

In the case of mammalian cells, the markers used can be for example sequences that code for the activity of DHFR, of cytosine-deaminase, of hygromycin-β-phosphotransferase (HPH), of puromycin-N-acetyl transferase (PAC), of thymidine kinase (TK) and of xanthine-guanine phosphoriboseultransferase (XGPRT).

Alternatively, sequences can be used that code for a counterselection marker, for example the sacB gene of *B. subtilis* or the F-plasmid ccdB-gene or colicin-release-gene such as the kil-gene for colicinE1.

Another example is the use of a fragment of the Mu phage as described in Schumann (1979) Mol. Gen. Genet. 174, 221-4. Other examples of such markers are described in Roberts et al. (1980) Gene 12, 123-7; Dean (1981) Gene 15, 99-102, Hennecke et al. (1982) Gene 19, 231-4 or Hashimoto-Gotoh et al. (1986) Gene 41, 125-8.

Additionally, sequences can be used that permit selection on the basis of the blue/white coloration after adding IPTG/X-GAL.

Additionally sequences can be inserted in the region between promoters $P_1$ and $P_2$, which make screening by PCR possible.

In one embodiment, expression vectors can be used that permit coexpression of the cloned sequence with a detectable marker. Said detectable marker can for example be a tag such as a His tag, a Poly-His tag, an MAT tag, a streptavidin tag, a streptavidin-binding tag, a GST tag, an antibody-binding tag, a Myc tag, a Swa11 epitope or a FLAG tag. In one embodiment they can also be fluorescent tags such as a GFP tag, a BFP tag or an RFP tag.

In a preferred embodiment the expression vector according to the invention has at least 70%, preferably at least 80%, more preferably at least 85%, and most preferably at least 90% and in particular at least 95% homology to <SEQ ID NO: 1>. Homology is preferably determined using the algorithm according to Smith & Waterman (J Mol Biol., 1981, 147(1), 195-7), using the BLOSUM62 matrix and values of 11.0 for the opening of a gap, or 1.0 for the widening of a gap.

Another aspect of the invention relates to an expression system comprising the expression vector described above and separately occurring regulatory sequences, which code for a regulator $R_1$ of $P_1$ and/or for a regulator $R_2$ of $P_2$. In this connection, "separately" means that the regulatory sequences are not located on the expression vector according to the invention, or one or more parts integrated into the host chromosome. Preferably the regulatory sequences are located on a vector (regulatory vector), which codes for a regulator $R_1$ of $P_1$ and/or for a regulator $R_2$ of $P_2$. Preferably $R_1$ is LacI and/or $R_2$ is AraC.

The regulatory vector according to the invention preferably codes for both regulators $R_1$ and $R_2$ of the two promoters $P_1$ and $P_2$, which are located on the expression vector according to the invention.

Possible regulatory vectors include, for example, plasmids, phage, cosmids, phasmids, fosmids, bacterial artificial chromosomes, yeast artificial chromosomes, viruses and retroviruses (for example vaccinia, adenovirus, adeno-associated virus, lentivirus, herpes-simplex virus, Epstein-Barr virus, fowlpox virus, pseudorabies, baculovirus) and vectors derived therefrom.

The regulatory vector or parts thereof can also be integrated into the genome.

Any other vector can be used for production of the regulatory vector according to the invention, provided it is replicable and capable of surviving in the selected system (host).

Preferably the regulatory vector is a plasmid (called "regulatory plasmid" within the scope of the invention).

Preferably the expression vector according to the invention is also a plasmid, so that the expression system according to the invention preferably comprises two plasmids: expression plasmid and regulatory plasmid.

In a preferred embodiment the regulatory plasmid comprises more by than the expression vector or the expression plasmid.

In one preferred embodiment the regulatory plasmid according to the invention is a low-copy plasmid (on average <100 plasmids per cell). In another preferred embodiment the regulatory plasmid according to the invention is a high-copy plasmid (on average ≥100 plasmids per cell).

The regulatory vector also contains a selection marker sequence. Preferably the selection marker sequence of the regulatory vector is different from the selection marker sequence of the expression vector.

The regulatory vector preferably serves for effective control both of $P_1$ and of $P_2$. It is then the ara promoter and the T7 promoter, therefore the regulatory vector is preferably a vector expanded by an araC-variation and a part of the ara-regulatory region, which additionally bears the structural gene for the LacI repressor.

AraC is the repressor/activator of the ara promoter, and LacI is the repressor of the T7 promoter.

The LacI repressor performs two functions. On the one hand it binds to regulatory elements between T7 promoter and transcription start (operator sequence lacO) and prevents the start of transcription. On the other hand, in a preferred embodiment, expression of the T7-RNA polymerase in the expression host is also under the control of a lacO operator sequence. For as long as the LacI repressor is bound to this operator sequence, expression of the T7-RNA polymerase itself is suppressed and therefore also does not transcribe any sequences that are under the control of the T7 promoter. IPTG ($I_1$) binds to the lad repressor, which is inactivated as a result and can no longer bind to the operator sequences lacO and so transcription of the T7-RNA polymerase itself, and of the genes located downstream of the T7 promoter is released.

This permits effective control of expression by IPTG- or L-arabinose-induction (inductor $I_1$ or inductor $I_2$). The expression vector according to the invention preferably comprises as cloning or expression component of the 2-component system on one side of the MCS, the T7-promoter/operator region, and on the other side the complete Ara-promoter-operator region (cf. FIG. 1).

In the literature, the ara-regulator AraC is generally expressed on the same plasmid as the target gene. This is preferably not so with the expression vector according to the invention. In this way a plasmid is obtained that is reduced in size to the maximum, which offers advantages in the bottleneck of ligation/transformation, as the achievable transformation rates and hence achievable library sizes are larger, the smaller the plasmid used. Instead, araC can be cloned into the T7-regulatory plasmid, where, like lacI, it is expressed independently of the expression plasmid. At the same time, the araC gene is preferably shortened, to ensure more efficient inductor binding. (Lee et al., (2007); Appl. Environ. Microbiol. 73, 5711-5715).

In a special embodiment the regulatory vector bears additionally at least one gene for a transfer-RNA of the host organism. Preferably these genes are selected from the group comprising argU, argW, ileX, gluT, leuW, proL, metT, thrT, tyrU, thrU and argX of *E. coli*, which recognize the codons AGG, AGA, AUA, CUA, CCC, GGA or CGG. Through the presence of these additional transfer-RNA genes, target genes that have a usage of the amino acid codons in their sequence different from *E. coli* (codon usage) can also be expressed at higher yield by the expression vector. This can occur in particular for eukaryotic genes (e.g. human) or genes from other groups of microorganisms (e.g. actinomycetes).

In another special embodiment the regulatory vector contains genes for one or more inhibitory proteins for one or more RNA polymerases. These one or more RNA polymerases are the RNA polymerase(s) that are used, i.e. the RNA polymerase of the host and/or an RNA polymerase foreign to the host, coexpressed in the host cell.

In yet another special embodiment, the expression system, preferably the regulatory vector, contains the gene lysS, which codes for the T7-lysozyme. The T7-lysozyme can bind to the T7-RNA polymerase and inactivate it. Through the presence of this gene in the host cell, basal expression of T7-RNA polymerase is suppressed and expression does not take place until expression of the T7-RNA polymerase is increased by adding an external inductor (IPTG) and is no longer capable of binding sufficient T7-lysozyme. In this way, even very toxic proteins can be expressed under the control of the T7 promoter. As economically important enzymes often present hydrolytic and therefore toxic activities (proteases, lipases etc.) this is of particular advantage.

Expression vector and regulatory plasmid are compatible according to the invention and can preferably be replicated simultaneously in the host, e.g. in *E. coli*. Reading of the T7 promoter in *E. coli* requires expression of T7-polymerase, for example as in *E. coli* BL21(DE3). The ara promoter does not require any *E. coli*-foreign polymerase.

Preferably the regulatory plasmid according to the invention comprises altogether at most 7000 bp, preferably at most 6500 bp, more preferably at most 6000 bp, and most preferably at most 5500 bp and in particular at most 5000 bp.

Especially preferably the regulatory plasmid according to the invention has at least 70% homology to <SEQ ID NO: 2>. The homology is preferably determined by the algorithm according to Smith & Waterman (J Mol Biol, 1981, 147(1), 195-7), using the BLOSUM62 matrix and values of 11.0 for the opening of a gap, or 1.0 for the widening of a gap.

Another aspect of the invention relates to a method of expression of DNA sequences using the expression vector or expression system described above comprising the steps
(i) optionally transfecting or transforming a suitable host organism with the regulatory plasmid;
(ii) cloning a DNA sequence or a DNA sequence mixture (library) into the expression vector between $P_1$ and $P_2$;
(iii) optionally transfecting or transforming the host organism obtained in (i) with regulatory plasmid with the constructs obtained in step (ii); and
(iv) inducing expression of the proteins encoded by the DNA sequences by adding the inductor $I_1$ and/or the inductor $I_2$.

The DNA sequence is preferably a constituent of a (meta)genome library. Genomic DNA sequences, extrachromosomal DNA sequences and cDNA sequences are included.

In one embodiment the cloning into the expression vector takes place by subcloning from another vector.

The terms "transfected" or "transformed" in the sense of the invention cover all methods of introducing nucleic acids into the host, e.g. including infection. The construct can be introduced in various ways, depending on the host used. Introduction of the construct into a prokaryotic host can for example take place by means of transformation, e.g. electroporation, transduction or transfection. Introduction of the construct into a eukaryotic host can, depending on the type of construct (expression vector), for example take place via calcium phosphate-DNA coprecipitation, DEAE-dextran-mediated transfection, polybrene-mediated transfection, electroporation, microinjection, liposome fusion, lipofection, viral infection, retroviral infection or ballistic methods.

According to the invention, the regulatory vector or at least the parts that encode the repressor can also be introduced into the host by these methods.

In one preferred embodiment of the method according to the invention, $I_1$ and $I_2$ are added successively. It was found, surprisingly, that in this way inhibition of the weaker promoter can be avoided.

In another preferred embodiment of the method according to the invention, $I_1$ and $I_2$ are added to spatially separate partial cultures of the organisms obtained and therefore the two promoters are induced individually. It was found, surprisingly, that mutual inhibition of the promoters can also be avoided in this way.

Therefore, according to the invention preferably spatially separate induction of reading of the same sequence takes place in different directions of reading, but not the successive or simultaneous induction of reading of different sequences.

Especially preferably $I_1$ is the inductor for $P_1$, but not for $P_2$, and/or $I_2$ is the inductor for $P_2$, but not for $P_1$.

Another aspect of the invention relates to a method of screening of DNA libraries using the expression vector or expression system described above comprising the method described above for expression of DNA sequences.

Preferably screening is carried out with respect to catalytic activity of the expressed proteins. Preferably it is catalytic activity of one of the following enzyme classes: 1. Oxidoreductases, 2. Transferases, 3. Hydrolases, 4. Lyases, 5. Isomerases and 6. Ligases. Preferred oxidoreductases are selected from the EC group comprising 1.1, 1.2, 1.3, 1.4, 1.5, 1.6, 1.7, 1.8, 1.9, 1.10, 1.11, 1.12, 1.13, 1.14, 1.15, 1.16, 1.17, 1.18, 1.19 and 1.97. Preferred transferases are selected from the EC group comprising 2.1, 2.2, 2.3, 2.4, 2.5, 2.6, 2.7, 2.8 and 2.9. Preferred hydrolases are selected from the EC group comprising 3.1, 3.2, 3.3, 3.4, 3.5, 3.6, 3.7, 3.8, 3.9, 3.10, 3.11 and 3.12. Preferred lyases are selected from the EC group comprising 4.1, 4.2, 4.3, 4.4, 4.5, 4.6 and 4.99. Preferred isomerases are selected from the EC group comprising 5.1, 5.2, 5.3, 5.4, 5.5 and 5.99. Preferred ligases are selected from the EC group comprising 6.1, 6.2, 6.3, 6.4 and 6.5. The EC nomenclature introduced by the International Union of Biochemistry and Molecular Biology (IUBMB) is known by a person skilled in the art. Information about this can be found on the website of the IUBMB.

Suitable assays for detecting a given catalytic activity are known by a person skilled in the art. They are preferably based on UV/VIS spectroscopy, fluorescence, luminescence or radioactivity. In this connection, reference may be made for example to J. L. Reymond, Enzyme Assays: High-throughput Screening, Genetic Selection and Fingerprinting, Wiley VCH, 2006 in its entirety.

Alternatively, however, screening based on binding affinities is also possible. For example, this can be the binding affinity to an antibody or to some other binding partner (for example a protein or a nucleic acid or a carbohydrate).

Screening based on functional assays that are suitable in each case, and known by persons skilled in the art, is also possible.

In one embodiment the selected sequence is identified by sequencing the cloned sequence.

In a special embodiment of the method, the host cell is multiplied and the expressed protein can be submitted to further steps such as purification and/or biochemical and/or functional characterization.

In a special embodiment these steps take place using the tags linked to the expressed protein. As tags, it is possible for example to use a His tag, a Poly-His tag, a MAT tag, a streptavidin tag, a streptavidin-binding tag, a GST tag, an antibody-binding tag, a Myc tag, a Swa11 epitope or a FLAG tag or fluorescent tags such as a GFP tag, a BFP tag or an RFP tag.

The preferred field of application of the expression vector according to the invention is as cloning and expression vector for the enzyme activity screening of genome and metagenome libraries. In fact, with (meta)genome libraries, high complexity (>$10^6$ clones) is necessary, so that already when they are being prepared, high cloning and transformation efficiency is decisive. Furthermore, the ideal screening vector must also enable efficient screening of large numbers of clones. In cluster screening, as in other screening assays, strong, controllable expression of the target proteins is essential. The expression vector according to the invention was specially developed for these requirements—high cloning efficiency combined with efficient, controllable expression.

In contrast to the systems known from the prior art, the expression vector according to the invention has two strong, plasmid-located promoters, which moreover are still controllable, which offers advantages in screening for slightly toxic proteins. In the case of slightly toxic proteins, in fact, the host organism, e.g. *E. coli*, tolerates the presence of these proteins only for a relatively short time. In such cases, controllable promoters make it possible for the gene that codes for these slightly toxic proteins to be "switched off" at first, until the host organism has multiplied sufficiently. Then the controllable promoters enable the gene to be "switched on", thus inducing production of the slightly toxic proteins for some time, before the expressed proteins exert their toxic action. In addition to the possible toxicity of a target protein, generally every additional expression of a recombinant protein represents a stress for the host organism (consumption of resources). Therefore as a rule it is always advantageous to switch on expression of the recombinant proteins only after reaching sufficiently strong multiplication.

With the two convergent promoters in the expression vector according to the invention, it is possible to cover both potential orientations and thus double the usable information content of the cloned DNA. The ORFs can be expressed independently of orientation and therefore their gene products can be screened on the basis of activity.

In addition to the great promoter strength, the separate induction of the two promoters is also advantageous, because in this way possible antisense RNA effects can be excluded.

The separately inducible promoters of the expression vector according to the invention offer advantages. A decrease in promoter strength, or expression efficiency of the ORFs read can thus be avoided.

Transcriptional interferences by convergent promoters had already been observed with eukaryotes. Thus, Callen et al. describe suppression of the weaker promoter by a factor of 5.6 with closely adjacent face-to-face promoters of different strength (Callen et al. (2004), Molecular Cell, 14, 647-56 B). Eszterhas et al. show that with a convergent promoter arrangement, the activity of two reporter genes is reduced almost to the background level (Eszterhas et al. (2002), Molecular and Cellular Biology 22, 469-79). This is sometimes attributed to disturbance of the binding properties in the promoter region. These results can be transferred to prokaryotes with limitations, taking into account that their transcription initiation differs from that of the eukaryotes.

The expression system according to the invention combines the small size of a conventional cloning vector with the expression possibilities of controllable expression vectors.

By using the two convergent promoters, the size of library that must be screened in order to cover a certain amount of DNA statistically, is halved. The separate induction of the promoters prevents possible transcriptional interference by antisense RNA, which is inevitably formed in simultaneous induction or a reduced transcription activity of the weaker promoter due to a higher transcription rate of the stronger promoter.

A high, easily controllable promoter strength is of decisive advantage in the cluster screening method, as the strong signals against the background are detected better and accordingly greater complexities can be screened than previously.

Therefore the expression system according to the invention is tailor-made for every kind of activity screening of banks with randomized fragmented (meta)genomic DNA, but in particular for cluster screening.

This is a method of iterative deconvolution of variant libraries, which has considerable advantages over conventional deconvolution methods.

In a preferred embodiment of such a method, shown schematically in FIG. 6, a library, preferably a (meta) genome library, is prepared (FIG. 6, Step a.)(i)). The library contains the individual variants "A", "B", "C" and "D". According to the invention, this library is transferred into a host (FIG. 6, Step a.)(ii)).

In Step b.) the clones of one partial library are divided into a first compartment (variants "A" and "B" in FIG. 6) and the clones of another partial library into a second compartment (variants "C" and "D" in FIG. 6).

During this dividing-up, it is not known which variants are put in which compartment. The compartments can for example be two adjacent wells on a first microtitre plate ("1st plate").

Now, in Step c.)(i), multiplication of the clones of the individual partial libraries takes place, preferably by growth of the organisms within the compartments on the 1st plate.

In a preferred embodiment, next, in Step c.)(ii), an aliquot of the multiplied organisms is preserved, preferably retaining the compartment allocation. For retaining the compartment allocation, for example a second microtitre plate ("2nd plate") can be used, wherein preferably the aliquot of the multiplied organisms, which is taken from the first compartment on the 1st plate, is transferred to the corresponding first compartment on the 2nd plate.

With the unpreserved part of the multiplied organisms, in Step c.)(iii) biomolecules are produced, wherein clones that contain variant "A" produce biomolecules "a"; clones that contain variant "B" produce biomolecules "b"; and so on. Typically, the biomolecules are proteins, which are expressed by the organisms. The host organisms are macerated. A person skilled in the art knows various methods for this, for example cell lysis with suitable chemicals or cell lysis by osmotic shock or by the use of shearing forces such as the "French-press" method. The result is decoupling of phenotype and genotype.

In Step c.)(iv), now in each case all of the biomolecules "a" and "b" contained in the first compartment and all of the biomolecules "c" and "d" contained in the second compartment are tested. This preferably takes place by screening for a particular biocatalytic activity (phenotype). In the example chosen, only all of the biomolecules contained in the first compartment "a" and "b" show the desired biocatalytic activity, which is shown symbolically with grey shading of the first compartment. From the observed phenotype, it is not possible to draw any direct conclusions about the genotype, as it is not outwardly apparent which of the biomolecules is responsible for the positive test, "a" or "b", and moreover it is not known from which variants the totality of the partial library is composed (cf. explanation Step b.) above).

The first compartment therefore contains biomolecules that fulfil the desired biocatalytic activity, and is selected in Step d.).

The procedure now preferably does not start from the selected partial library in the first compartment as such, but from the preserved partial library in the corresponding first compartment on the 2nd plate (indicated by a dashed line). It is also possible to perform the preservation of the partial libraries directly in the 1st plate. In Step e.) the preserved partial library, which comprises the clones of variants "A" and "B", is diluted and divided up. The clones of variants "A" and "B" are transferred respectively to different compartments. The compartments can for example be two wells on a third microtitre plate ("3rd plate").

Finally, in Step f.), Steps c.) to e.) are repeated until in each compartment only at most one variant of the gene sequence coding for the biomolecule is still contained. Under these preconditions, it is then possible to draw direct conclusions about the genotype from the observed phenotype, as all biomolecules contained in the compartment go back to an individual, separated clone.

In a special embodiment of the method according to the invention for screening DNA libraries, the DNA library comprises $10^3$ to $10^{25}$ different sequences. The DNA library can for example comprise $10^3$ to $10^5$, $10^5$ to $10^{10}$, $10^{10}$ to $10^{15}$, $10^{15}$ to $10^{20}$ or even $10^{20}$ to $10^{25}$ different sequences.

According to the invention, Steps c.) to e.) can be repeated, and a person skilled in the art is able, taking into account the size of the library, to determine a number of repetitions appropriate to the particular circumstances.

According to the invention, Steps c.) to e.) can for example be repeated at least 1×, preferably at least 2×, preferably at least 3×, more preferably at least 5×, more preferably at least 10× until individual sequences are individualized.

In a preferred embodiment, after the first division of the library into compartments of the 1st plate, each compartment contains on average at least 10, preferably at least 20, more preferably at least 40, and most preferably at least 100 and in particular at least 1000 different variants. In one embodiment, the partial libraries therefore comprise, in the first round, preferably ≥10, more preferably ≥$10^2$, even more preferably ≥$10^3$ sequences.

The following examples serve for explanation of the invention, but are not intended to be limiting.

Figure 1:
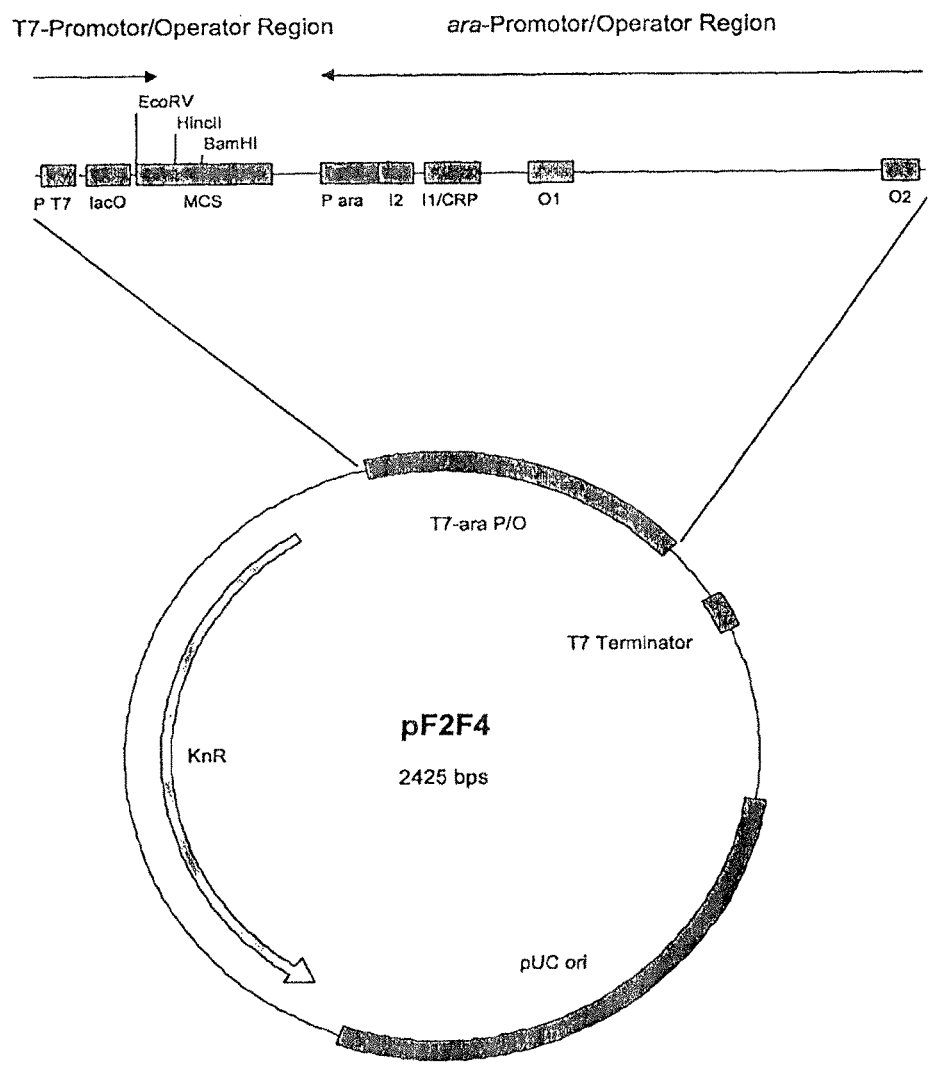
FIG. 1 shows pF2F4, a preferred embodiment of an expression vector according to the invention with <SEQ. ID. NO: 1>. It is an expression vector for *E. coli*, in which two strong promoters flank the multiple cloning site. The promoters are convergent, i.e. their reading directions converge towards each other (face-to-face). The promoters that are inducible independently of one another are a T7 promoter and an arabinose promoter.

In the following examples, pF2F4 was used, an expression vector for *E. coli*, in which two strong promoters flank the multiple cloning site (cf. FIG. 1). The promoters are convergent, i.e. their reading directions converge towards each other (face-to-face). The promoters that are inducible independently of one another are a T7 promoter and an arabinose promoter. DNA cloned into this vector can thus be transcribed from both sides, which halves the number of clones to be screened. The strong vector-supported transcription is independent of insert-coded promoters and thus increases the hit rate.

Example 1

Figure 2:
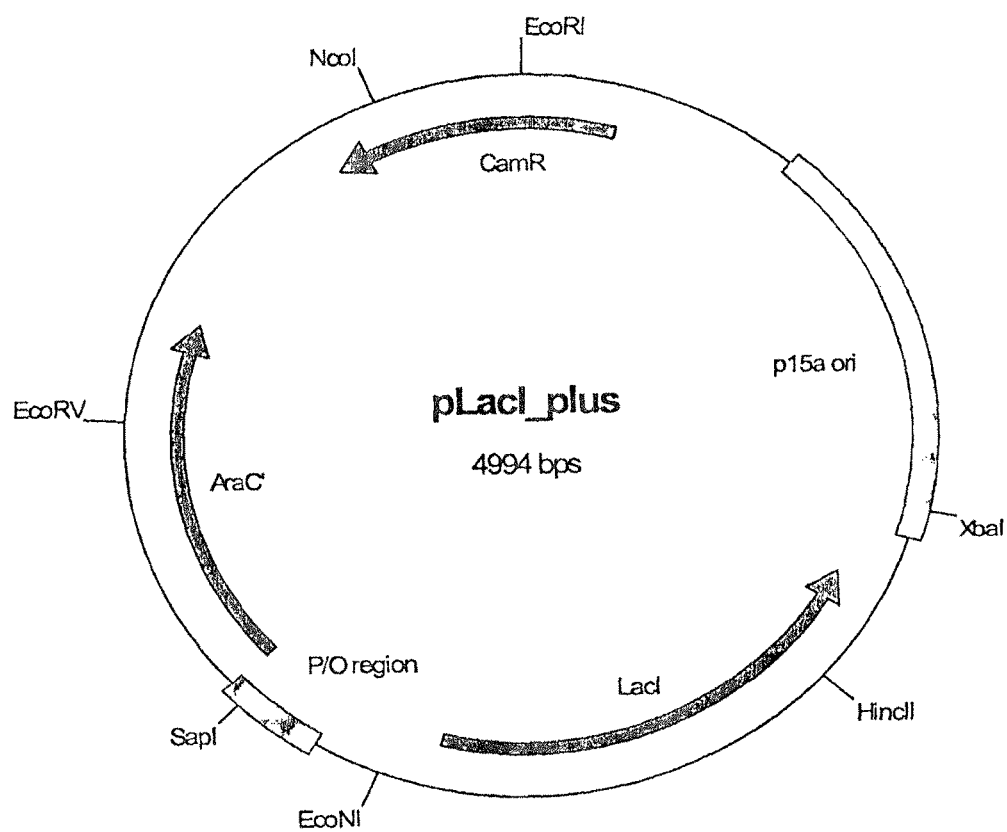
FIG. 2 shows the regulatory plasmid pLac+ with <SEQ. ID. NO: 2>, with which, according to the invention, the host organism is preferably transformed together with the expression vector.
Figure 3:
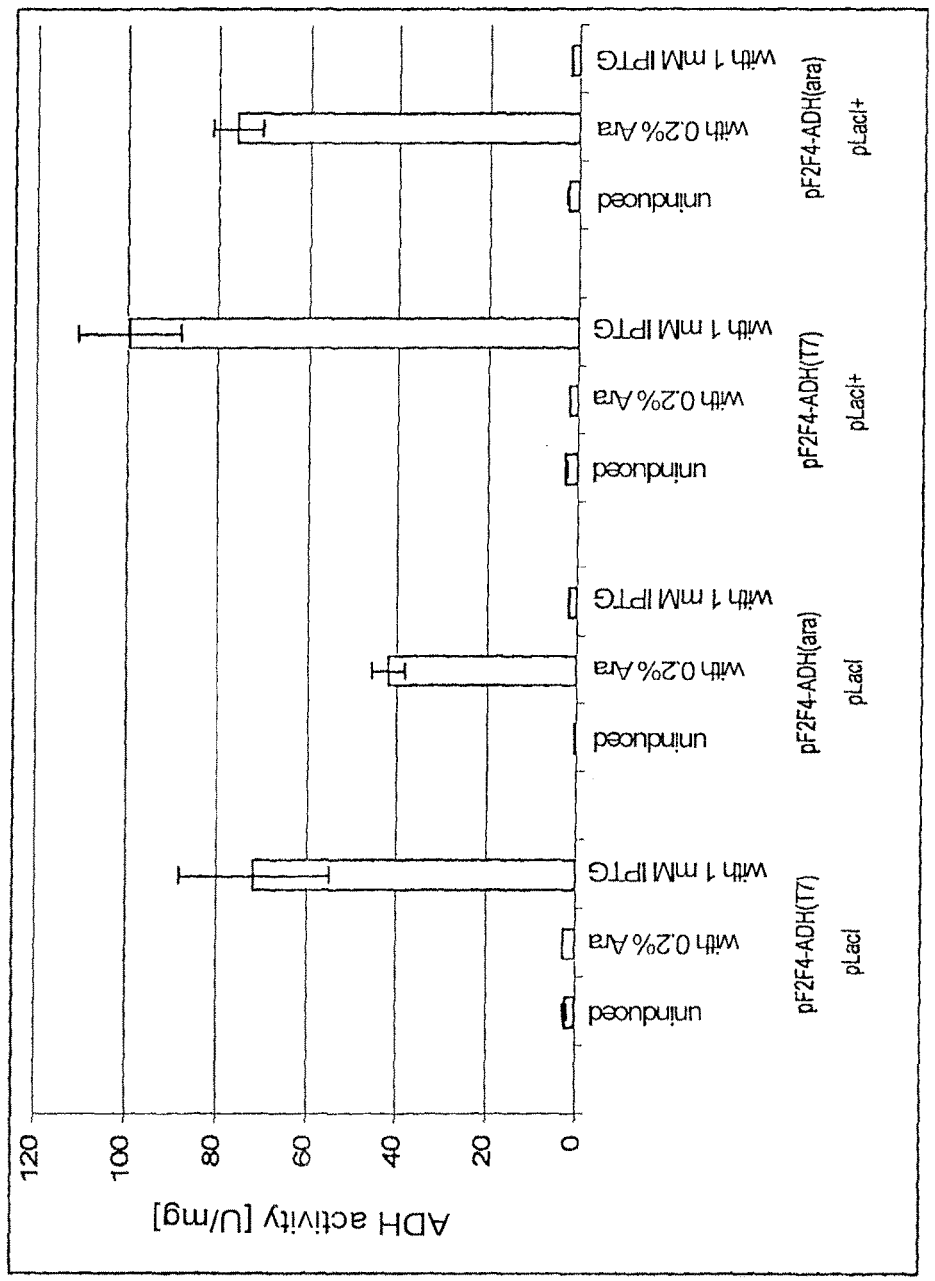
FIG. 3 shows, in connection with example 1, pF2F4 with variously oriented alcohol dehydrogenase as reporter gene in *E. coli* BL21 (DE3) cells, in which pLacI or pLacI+ is propagated simultaneously. All measurements of T7 induction with 1% glucose in the medium, of Ara induction without further glucose addition.

The promoter strength of the ara or T7 promoter in pF2F4 was investigated in various situations using a reporter gene. The data show that pF2F4, in conjunction with the regulatory plasmid pLacI+ (cf. FIG. 2) is optimum for use as the expression plasmid. The reporter gene used was an alcohol dehydrogenase (ADH), which was inserted in both possible orientations. The gene was under the control of the ara promoter or of the T7 promoter, respectively. Only the combination of regulatory plasmid encoded LacI and AraC with the pF2F4 plasmid leads to maximum possible expression starting from the Ara promoter and from the T7 promoter (FIG. 3).

Figure 4B:
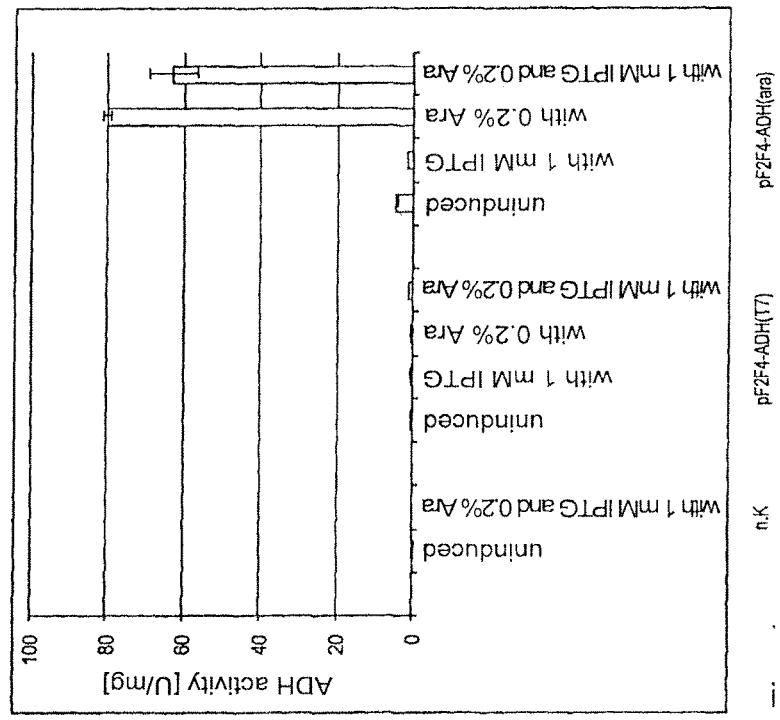
FIG. 4B shows ADH activity, in connection with pF2F4 with variously oriented alcohol dehydrogenase as reporter gene in *E. coli* DH10B. The pLacI+ plasmid was coexpressed in all assays.
Figure 4A:
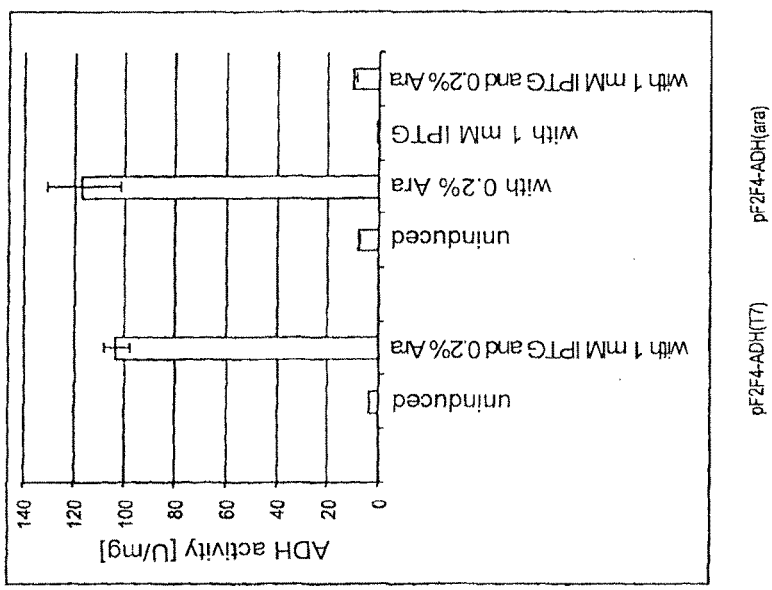
FIG. 4A shows ADH activity, in connection with example 1, pF2F4 with variously oriented alcohol dehydrogenase as reporter gene in *E. coli* BL21.

The ara promoter activity is lowered in the BL21 strain with simultaneous T7 induction to approx. 10% of the initial activity (FIG. 4A). The possibility of this effect being based on competitive inhibition of the regulator AraC by IPTG can be ruled out, as the inhibition is only observed in *E. coli* BL21(DE3). No significant decline in ara promoter activity is observed in an *E. coli* strain without chromosomal T7-polymerase (DH10B) (FIG. 4B). Here, the T7-activity is switched off to the greatest extent. The minimal activity still occurring is the basal activity of the T7 promoter, which even in *E. coli* without chromosomal T7-polymerase is recognized to a slight extent by the host organism's own polymerase (FIG. 4).

Example 2—Example of Application of pF2F4: Screening for Esterase/Lipase Activity in a Metagenome Bank A metagenome library set up in pF2F4 was screened for esterase/lipase-activity, using the cluster screening method (Greiner-Stoeffele, T., Struhalla, M., 2005, WO 2004/002386). The hit rate was compared with that of a metagenome bank cloned into the conventional pUC-vector. The target activity was an activity that is readily detectable with an established enzyme assay, and whose occurrence in metagenome banks has been described sufficiently in the literature.

1. Preparation of the Metagenome Bank

For the metagenome banks used, metagenomic DNA (mgDNA) was isolated from the contents of a sheep's rumen by direct lysis (Zhou. J.; Bruns, M. A.; Tiedje, J. M. (1996): DNA recovery from soils of diverse composition. Appl. Environ. Microbiol; 62(2): 316-22). For preparing the metagenome bank in pF2F4, the mgDNA was then partially digested with the restriction enzyme AluI and ligated by standard methods into the vector pF2F4, blunt-end cut with HindI and EcoRV and dephosphorylated (Sambrook, J., Fritsch, E. F., Maniatis, T., (1989). Molecular cloning: A laboratory manual. Cold Spring Laboratory Press 2nd Ed. Cold Spring Harbor, USA).

For preparing the metagenome bank in pUCWhite, a pUC18 derivative, the mgDNA was digested with Bsp143I and also ligated by standard methods into the vector pUCWhite that had been cut with BamHI and dephosphorylated.

For multiplying the libraries, electrocompetent *E. coli* DH10B cells were transformed with the libraries by electroporation. The pF2F4 library had an average insert size of 3.7 kb with inserts of 2.4-4.6 kb and a size of $2.9 \times 10^6$ individual clones. The pUC library had an average insert size of 3.5 kb with inserts of 1.9-5.9 kb and a size of $3.9 \times 10^6$ individual clones. After verification of quality, the libraries were isolated by preparation in the Midi-Scale (Qiagen, Hilden) from *E. coli* DH10B and electrocompetent cells of the expression strain *E. coli* BL21 (DE3) were transformed with 720 ng (pF2F4-rumen) or 200 ng (pUC-rumen) of the library. The expression strain transformed with the pF2F4 library additionally contained the regulatory plasmid pLacI+.

2. Cell Propagation

Screening of the metagenome banks was performed using the cluster screening method (Greiner-Stoeffele, T., Struhalla, M., 2005, WO 2004/002386). In this high-throughput method, mixed cultures (clusters) of up to 1000 individual clones (here 300) are applied in the initial screenings. The clusters, to which the hits found in this first screening step relate, are diluted and screened again, until single clone level is reached. The single clones obtained are then characterized enzymatically and by methods of molecular biology. In this example of application, only the initial screening is carried out. All propagations were carried out in conditions optimized for the respective expression system. As the pF2F4 vector possesses two convergent vectors, and these were to be induced separately, from the pF2F4 library, two main cultures from a preculture were inoculated with standard media.

2.a Preculture

Cultivation of the libraries in the expression strain was carried out in the 96-well format in deep-well plates. A preculture was grown first. Each well was inoculated with ~300 individual clones of a metagenome bank, except that well A1 remained uninoculated as a control. At the same time, aliquots of the inoculated culture medium were plated out in order to verify the clone number. For the pF2F4-rumen bank, 278 individual clones/well were detected and for the pUC-rumen bank 300 individual clones/well. Preculture was carried out in 400 µl of medium. During preculture of the pUC library, 1% glucose and 100 µg/ml ampicillin were added to the medium. During preculture of the pF2F4 library, 0.5% glucose and 50 µg/ml kanamycin and 37 µg/ml chloramphenicol were added to the medium. Propagation took place overnight at 37° C. and 1000 rpm in a rotary shaker.

2.b Main Culture

For the main culture of the pF2F4 library, two deep-well plates were inoculated in parallel, as the convergent promoters pAra and pT7 were to be induced separately. The main cultures of the pUC library and the part of the pF2F4 library to be induced later with IPTG were propagated in 1.2 ml of medium with 0.5% glucose and the corresponding antibiotics (ampicillin for the pUC library and kanamycin and chloramphenicol for the pF2F4 library). The part of the pF2F4 library to be induced with arabinose was propagated in the same medium without glucose. The main cultures were inoculated in each case with 30 µl of preculture, with well A1 remaining uninoculated as control. After incubation at 30° C. and 1000 rpm, the cultures were induced on reaching an OD of 0.7. For this, 1 mM IPTG was added to the pUC library and 0.5 mM IPTG or 0.2% L-arabinose was added to the two pF2F4 plates. Cultivation was continued overnight at 30° C. and 1000 rpm.

3. Cell Harvesting and Lysis

The expression cultures grown overnight were centrifuged at 4000×g. The culture supernatant was removed, to be used additionally to the cell extract in the enzyme assay. The cell pellets were digested in CellLytic buffer to obtain the cell extract. For this, they were each resuspended in 200 µl CellLytic buffer and incubated for 30 min at 37° C. Then the cell debris was centrifuged at 4000×g for 15 min at 4° C. CellLytic buffer:

1 ml CellLytic B Cell Lysis Reagent (Sigma-Aldrich, Steinheim)

1 mg lysozyme (Applichem, Darmstadt)

1 µl benzonase (Sigma-Aldrich)

to 10 ml 50 mM K-phosphate buffer pH 8.

4. Enzyme Activity Assay

The activity assays were carried out with pNP-caprylate, an artificial substrate, for which a fatty acid consisting of 8 carbon atoms is derivatized via an ester bond with para-nitrophenol. During degradation, p-nitrophenolate is released, which can be detected at 405 nm. In each case 5 µl of cell extract or 5 µl of culture supernatant was mixed with 95 µl of assay buffer in flat-bottomed 96-well plates and incubated for up to 12 h at room temperature. If the background values were too high, the cell extracts were diluted 1:10 in KP8T buffer. Then the absorption at 405 nm was determined in a microplate reader (Infinite 200, Tecan, Crailsheim).

Composition of Assay Buffer:
200 µl pNP-caprylate (Sigma-Aldrich)
to 20 ml KP8T buffer
KP8T buffer:
23.5 ml 1 M K2HPO4
1.5 ml 1 M KH2PO4
2.5 ml 20% Triton X-100
to 500.0 ml AquaMP
pH 8.0.

5. Evaluation

Wells were assessed as a hit for which the Z factor was >4, with Z defined as follows:

$$Z = (\text{absorption increase of the well} - \text{average of the absorption increase of the whole 96-well plate}) / \text{standard deviation of the average of the absorption increase of the whole 96-well plate}.$$

Results

From the pF2F4-rumen library, ~26400 clones with a total insert size of 97.7 Mb were screened for esterase/lipase activity. Both the culture supernatants and the cell extracts of both induction batches were examined. There were 10 non-redundant hits, which corresponds to a hit rate of 1 hit/9.8 Mb. Hits that appeared in several measurements were only included once in the overall balance.

Figure 5:
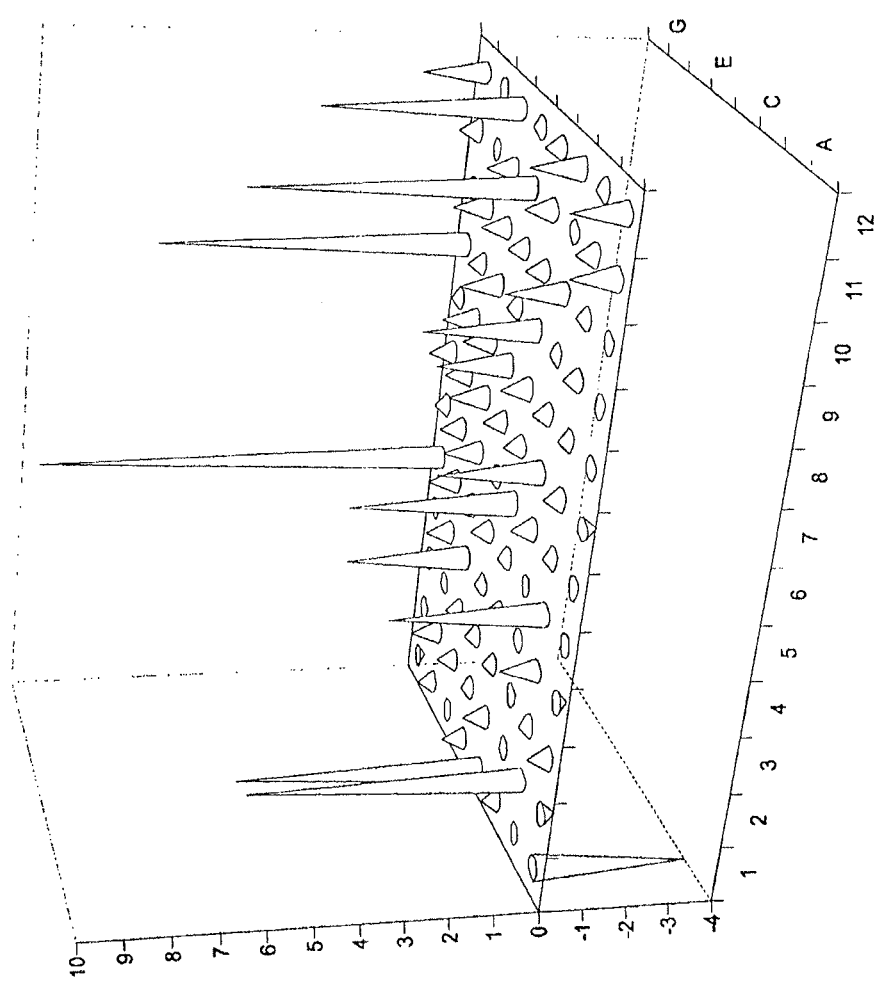
FIG. 5 shows, in connection with example 2, the hit distribution after 3 h incubation time in the IPTG-induced cell extract of the rumen library in pF2F4. A1 is uninoculated as control.

From the pUC-rumen library, ~28500 clones with a total insert size of 99.8 Mb were screened for esterase/lipase activity. Both the culture supernatants and the cell extracts were examined. There was 1 hit, which corresponds to a hit rate of 1 hit/99.8 Mb. Therefore, for the metagenome library in pF2F4 there is a ~10 times higher hit rate than for the pUC library. The hits are summarized in Table 1, and FIG. 5 shows the hit distribution in the cell lysis of the pF2F4 library induced with IPTG.

TABLE 1

Esterase/lipase hits in the libraries after up to 24 h of incubation with pNP-caprylate

|  | pF2F4-rumen (97 Mb screened) | pUC-rumen (95 Mb screened) |
|---|---|---|
| Culture supernatants, IPTG-induced | 1 | 0 |
| Cell lysis, IPTG-induced | 6 | 1 |
| Culture supernatants, arabinose-induced | 0 | — |
| Cell lysis, arabinose-induced | 5 | — |
| Total | 12 | 1 |
| Total minus hits occurring several times | 10 | 1 |

Hit Rate Comparison

In order to show that the 2-promoter system in pF2F4 is superior to a simple lac promoter, a hit rate comparison was carried out. For this, a test screening for lipase/esterase activity was carried out with pNP-caprylate as substrate in cluster screening with ~300 clones/well. The libraries used comprise fragmented metagenomic DNA, which was obtained from sheep rumen flora and was cloned both in pF2F4 and in pUCwhite, a pUC18 derivative. The average insert lengths were 3.5 kb (pUC-rumen) or 3.7 kb (pF2F4-rumen). In the comparative screening, 101 Mb or 99 Mb of cloned DNA was therefore covered. In this test screening it was found that by a combination of strong promoters and promoter convergence, with the same insert-DNA and screening method, a hit rate (1/9.7 Mbp to 1/92 Mbp) higher by a factor of 9.5 can be achieved relative to a one-sided lac promoter system (pUC vector). As only double the hit rate would be expected from the convergent arrangement of the promoters, the rest of the increase in hit rate must be attributable to the promoter strength.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations within the scope of the appended claims and equivalents thereof.

The invention claimed is:

1. A method of expressing a DNA sequence or a mixture of DNA sequences comprising:
   (i) providing an expression system, comprising an expression vector and a separate regulatory vector,
   the expression vector comprising:
   two mutually independently inducible, convergent promoters $P_1$ (promoter 1) and $P_2$ (promoter 2),
   wherein between $P_1$ and $P_2$,
   an insertion sequence, positioned downstream of $P_1$ and downstream of $P_2$, configured so that the expression of a DNA sequence cloned into the insertion sequence is transcribed either via $P_1$ or $P_2$; wherein the insertion sequence comprises a polylinker and/or an integration sequence adapted to facilitate integration of the DNA sequence by recombination; and
   the regulatory vector comprising:
   a sequence encoding a first regulator ($R_1$) of the first promoter and/or a second regulator ($R_2$) of the second promoter,
   (ii) cloning the DNA sequence into the polylinker and/or the integration sequence of the expression vector to obtain a recombinant expression vector;
   (iii) subsequently transfecting or transforming the host organism comprising the regulatory vector with the recombinant expression vector obtained in (ii); and
   (iv) inducing expression of the proteins encoded by the DNA sequence by adding a first inductor ($I_1$) inducing an activation of the $R_1$ and/or adding a second inductor ($I_2$) inducing the activation of the $R_2$, wherein the expression vector without a DNA molecule cloned into the insertion sequence comprises not more than 3000 base pairs.

2. The method according to claim 1, wherein the $I_1$ and the $I_2$ are added to spatially separate partial cultures of the host organism obtained in (iii).

3. A method of screening a DNA library for a DNA molecule expressing a molecule having an activity of interest comprising:
   (a) providing an expression system comprising;
   an expression vector and a regulatory vector,
   the expression vector comprising:
   two mutually independently inducible, convergent promoters $P_1$ (first promoter) and $P_2$ (second promoter 2),
   wherein between $P_1$ and $P_2$, an insertion sequence is positioned downstream of $P_1$ and downstream of $P_2$, configured so that the expression of a DNA sequence cloned into the insertion sequence is transcribed either via $P_1$ or $P_2$,
   wherein the insertion sequence comprises a polylinker and/or an integration sequence adapted to facilitate integration of the DNA sequence by recombination; and
   the regulatory vector comprising:
   a sequence encoding a first regulator ($R_1$) of the $P_1$ and/or a second regulator ($R_2$) of the $P_2$;
   (b) cloning DNA molecules of the DNA library into the insertion sequence of the expression vector to produce a population of expression vectors comprising cloned DNA molecules,
   (c) transforming or transfecting a host cell population with the population of expression vectors of step (b) wherein the host cell population comprises the regulatory vector,
   (d) expressing the DNA molecule cloned into the insertion sequence by inducing expression of the $R_1$ by adding a first inductor ($I_1$) and/or the $R_2$ by adding a second inductor ($I_2$), and
   (e) screening the host cells for the activity of interest, wherein the expression vector without a DNA molecule cloned into the insertion sequence comprises not more than 3000 base pairs.

4. The method according to claim 3, wherein the activity of interest is a catalytic activity of a protein produced by the expression of the DNA molecule cloned into the insertion sequence.

5. The method according to claim 3, wherein the regulatory vector codes for a Laci regulator and/or for an AraC regulator.

6. The method according to claim 3, wherein the regulatory vector further comprises at least one gene for transfer-RNA of a host organism.

7. The method according to claim 6, wherein said gene for the transfer-RNA is selected from the group consisting of argU, argW, ileX, gluT, leuW, proL, metT, thrT, tyrU, thrU and argX of E. coli, which recognize the codons AGG, AGA, AUA, CUA, CCC, GGA or CGG.

8. The method according to claim 3, wherein the regulatory vector contains the gene LysS for the T7 lysozyme.

9. The method according to claim 3, wherein the $R_1$ and the $R_2$ are activated in step (d) in separate partial cultures of the transformed or transfected host cell population.

10. The method according to claim 3, wherein the $P_1$ is a T7 promoter and/or the $P_2$ is an ara promoter.

11. The method according to claim 3, wherein the expression vector codes for a first terminator ($T_1$) of the $P_1$ in reading direction of the $P_1$ downstream of the insertion sequence and/or for a second terminator ($T_2$) of the $P_2$ in reading direction of the $P_2$ downstream of the insertion sequence.

12. The method according to claim 11, wherein the $T_1$ is a T7 terminator and/or the $T_2$ is a terminator for the host RNA polymerase; or vice versa.

13. The method according to claim 11, wherein an additional gene lies between the $P_1$ and its $T_1$ in the reading direction of the $P_1$; or an additional gene lies between the $P_2$ and its $T_2$ in the reading direction of the $P_2$.

14. The method according to claim 1, wherein the regulatory vector or parts thereof are integrated into a genome of the host organism.

15. The method according to claim 1, wherein the regulatory vector codes for a Lad regulator and/or for an AraC regulator.

16. The method according to claim 1, wherein the regulatory vector further comprises at least one gene for transfer-RNA of a host organism.

17. The method according to claim 16, wherein said gene for transfer-RNA is selected from the group consisting of argU, argW, ileX, gluT, leuW, proI, metT, thrT, tyrU, thrU and argX of *E. coli*, which recognize the codons AGG, AGA, AUA, CUA, CCC, GGA or CGG.

18. The method according to claim 1, wherein the regulatory vector comprises gene LysS for T7 lysozyme.

19. The method according to claim 1, wherein the $P_1$ is a T7 promoter and/or the $P_2$ is an ara promoter.

20. The method according to claim 1, wherein the expression vector further codes for a first terminator ($T_1$) of the $P_1$ in reading direction of the $P_1$ downstream of the insertion sequence and/or for a second terminator ($T_2$) of the $P_2$ in reading direction of the $P_2$ downstream of the insertion sequence.

21. The method according to claim 20, wherein the first terminator is a T7 terminator and/or the second terminator is a terminator for the host RNA polymerase or vice versa.

22. The method according to claim 20, wherein an additional gene lies between the first promoter and the first terminator in the reading direction of the first promoter; or an additional gene lies between the second promoter and the second terminator in the reading direction of the second promoter.

23. The method according to claim 21, wherein an additional gene lies between the first promoter and the first terminator in the reading direction of the first promoter; or an additional gene lies between the second promoter and the second terminator in the reading direction of the second promoter.

24. The method according to claim 1, wherein more than one expression vector is provided each expressing a sequence of the mixture of DNA sequences.

25. The method according to claim 1, wherein the host organism is prior to the cloning in (ii) transfected or transformed with the regulatory vector.

26. The method according to claim 1, wherein $I_1$ is an inductor for $P_1$, but not for $P_2$ and/or $I_2$ is an inductor for $P_2$, but not $P_1$.

27. The method according to claim 14, wherein $I_1$ is an inductor for $P_1$, but not for $P_2$ and/or $I_2$ is an inductor for $P_2$, but not $P_1$.

28. The method according to claim 3, wherein the host organism is prior to the cloning in (b) transfected or transformed with the regulatory vector.

29. The method according to claim 3, wherein the regulatory vector or parts thereof are integrated into a genome of the host organism.

* * * * *

UNITED STATES PATENT AND TRADEMARK OFFICE
CERTIFICATE OF CORRECTION

PATENT NO. : 10,196,645 B2
APPLICATION NO. : 14/992723
DATED : February 5, 2019
INVENTOR(S) : Thomas Greiner-Stoeffele et al.

Page 1 of 1

It is certified that error appears in the above-identified patent and that said Letters Patent is hereby corrected as shown below:

In the Specification

In Column 2, Line 32, please delete "on" and insert -- ori --, therefor.

In Column 5, Line 29, please delete "on" and insert -- ori --, therefor.

In Column 5, Line 33, please delete "on" and insert -- ori --, therefor.

In Column 10, Line 37, please delete "by" and insert -- bp --, therefor.

In Column 10, Line 38, please delete "by" and insert -- bp --, therefor.

In Column 12, Line 49, please delete "by" and insert -- bp --, therefor.

In Column 12, Line 50, please delete "by" and insert -- bp --, therefor.

In Column 16, Line 66, please delete "by" and insert -- bp --, therefor.

In the Claims

In Column 37, Line 5, Claim 15, please delete "Lad" and insert -- Laci --, therefor.

Signed and Sealed this
Twenty-first Day of May, 2019

Andrei Iancu
*Director of the United States Patent and Trademark Office*

SEQUENCE LISTING

```
<160> NUMBER OF SEQ ID NOS: 5

<210> SEQ ID NO 1
<211> LENGTH: 2425
<212> TYPE: DNA
<213> ORGANISM: Artificial Sequence
<220> FEATURE:
<223> OTHER INFORMATION: Cloning Vector

<400> SEQUENCE: 1
cgaattcgct agcccaaaaa aacgggtatg gagaaacagt agagagttgc gataaaaagc      60
gtcaggtagc atccgctaat cttatggata aaaatgctat ggcatagcaa agtgtgacgc     120
cgtgcaaata atcaatgtgg actttctgc cgtgattata gacacttttg ttacgcgttt     180
ttgtcatggc tttggtcccg ctttgttaca gaatgctttt aataagcggg gttaccggtt    240
```

```
tggttagcga agaagagccag taaaagacgc agtgacggca atgtctgatg taatatggac      300
aattggtttc ttctcagaca attgacggct tgacggagta gcatagggtt tgcagaatcc      360
ctgcttcgtc catttgacag gcacattatg cataacccc ttggggcctc taaacgggtc       420
ttgaggggtt ttttgcttga taagctgtca aacatgagca gatcctctac gccggacgca      480
tcgtggccct gcattaatga atcggccaac gcgcggggag aggcggtttg cgtattgggc      540
gctcttccgc ttcctcgctc actgactcgc tgcgctcggt cgttcggctg cggcgagcgg      600
tatcagctca ctcaaaggcg gtaatacggt tatccacaga atcaggggat aacgcaggaa      660
agaacatgtg agcaaaaggc cagcaaaagg ccaggaaccg taaaaaggcc gcgttgctgg      720 cgttttttcca taggctccgc cccctgacg agcatcacaa aaatcgacgc tcaagtcaga     780
ggtggcgaaa cccgacagga ctataaagat accaggcgtt tccccctgga agctccctcg      840
tgcgctctcc tgttccgacc ctgccgctta ccggatacct gtccgccttt ctcccttcgg      900
gaagcgtggc gctttctcat agctcacgct gtaggtatct cagttcggtg taggtcgttc      960
gctccaagct gggctgtgtg cacgaacccc ccgttcagcc cgaccgctgc gccttatccg     1020
gtaactatcg tcttgagtcc aacccggtaa gacacgactt atcgccactg gcagcagcca     1080
ctggtaacag gattagcaga gcgaggtatg taggcggtgc tacagagttc ttgaagtggt     1140
ggcctaacta cggctacact agaaggacag tatttggtat ctgcgctctg ctgaagccag     1200
ttaccttcgg aaaaagagtt ggtagctctt gatccggcaa acaaaccacc gctggtagcg     1260
gtggtttttt tgtttgcaag cagcagatta cgcgcagaaa aaaaggatct caagaagatc     1320
ctttgatctt ttctacgggg tctgacgctc agtggaacga aaactcacgt taagggattt     1380
tggtcatgaa ttaattctta gaaaaactca tcgagcatca aatgaaactg caatttattc     1440
atatcaggat tatcaatacc atattttga aaaagccgtt tctgtaatga aggagaaaac      1500
tcaccgaggc agttccatag gatggcaaga tcctggtatc ggtctgcgat tccgactcgt     1560
ccaacatcaa tacaacctat taatttcccc tcgtcaaaaa taaggttatc aagtgagaaa     1620
tcaccatgag tgacgactga atccggtgag aatggcaaaa gtttatgcat ttctttccag     1680
acttgttcaa caggccagcc attacgctcg tcatcaaaat cactcgcatc aaccaaaccg     1740
ttattcattc gtgattgcgc ctgagcgaga cgaaatacgc ggtcgctgtt aaaaggacaa     1800
ttacaaacag gaatcgaatg caaccggcgc aggaacactg ccagcgcatc aacaatattt     1860
tcacctgaat caggatattc ttctaatacc tggaatgctg ttttcccggg gatcgcagtg     1920
gtgagtaacc atgcatcatc aggagtacgg ataaaatgct tgatggtcgg aagaggcata     1980
aattccgtca gccagtttag tctgaccatc tcatctgtaa catcattggc aacgctacct     2040
ttgccatgtt tcagaaacaa ctctggcgca tcgggcttcc catacaatcg atagattgtc     2100
gcacctgatt gcccgacatt atcgcgagcc catttatacc catataaatc agcatccatg     2160
ttggaattta atcgcggcct agagcaagac gtttcccgtt gaatatggct catactcttc     2220 cttttttcaat attattgaag catttatcag ggttattgtc tcatgagcgg atacatattt    2280
gaatgtattt agaaaaataa acaataggg gttccgcgca cattacgtca ttaatacgac      2340
tcactatagg ggaattgtga gcggataaca attcccgatat catgtgcctg caggtcgact    2400
ctagaggatc cccgggtacc gagct                                            2425
```

<210> SEQ ID NO 2
<211> LENGTH: 4994
<212> TYPE: DNA
<213> ORGANISM: Artificial Sequence
<220> FEATURE:
<223> OTHER INFORMATION: Cloning Vector

<400> SEQUENCE: 2

```
gaattccgga tgagcattca tcaggcgggc aagaatgtga ataaaggccg gataaaactt      60
gtgcttattt ttctttacgg tctttaaaaa ggccgtaata tccagctgaa cggtctggtt     120
ataggtacat tgagcaactg actgaaatgc ctcaaaatgt tctttacgat gccattggga     180
tatatcaacg gtggtatatc cagtgatttt tttctccatt ttagcttcct tagctcctga     240
aaatctcgat aactcaaaaa atacgcccgg tagtgatctt atttcattat ggtgaaagtt     300
ggaacctctt acgtgccgat caacgtctca ttttcgccaa aagttggccc agggcttccc     360
ggtatcaaca gggacaccag gatttattta ttctgcgaag tgatcttccg tcacaggtat     420
ttattcggcg caaagtgcgt cgggtgatgc tgccaactta ctgatttagt gtatgatggt     480
gtttttgagg tgctccagtg gcttctgttt ctatcagctg tccctcctgt tcagctactg     540
acggggtggt gcgtaacggc aaaagcaccg ccggacatca gcgctagcgg agtgtatact     600
ggcttactat gttggcactg atgagggtgt cagtgaagtg cttcatgtgg caggagaaaa     660
aaggctgcac cggtgcgtca gcagaatatg tgatacagga tatattccgc ttcctcgctc     720
actgactcgc tacgctcggt cgttcgactg cggcgagcgg aaatggctta cgaacggggc     780
ggagatttcc tggaagatgc caggaagata cttaacaggg aagtgagagg gccgcggcaa     840
agccgttttt ccataggctc cgcccccctg acaagcatca cgaaatctga cgctcaaatc     900
agtggtggcg aaacccgaca ggactataaa gataccaggc gtttccctg gcggctccct     960
cgtgcgctct cctgttcctg cctttcggtt taccggtgtc attccgctgt tatggccgcg    1020
tttgtctcat tccacgcctg acactcagtt ccgggtaggc agttcgctcc aagctggact    1080
gtatgcacga accccccgtt cagtccgacc gctgcgcctt atccggtaac tatcgtcttg    1140
agtccaaccc ggaaagacat gcaaaagcac cactggcagc agccactggt aattgattta    1200
gaggagttag tcttgaagtc atgcgccggt taaggctaaa ctgaaaggac aagttttggt    1260
gactgcgctc ctccaagcca gttacctcgg ttcaaagagt tggtagctca gagaaccttc    1320
gaaaaaccgc cctgcaaggc ggttttttcg ttttcagagc aagagattac gcgcagacca    1380
aaacgatctc aagaagatca tcttattaat cagataaaat atttctagat ttcagtgcaa    1440
tttatctctt caaatgtagc acctgaagtc agccccatac gatataagtt gtaattctca    1500
tgttagtcat gccccgcgcc caccggaagg agctgactgg gttgaaggct ctcaagggca    1560
tcggtcgaga tccggtgcc taatgagtga gctaacttac attaattgcg ttgcgctcac    1620
tgcccgcttt ccagtcggga aacctgtcgt gccagctgca ttaatgaatc ggccaacgcg    1680
cggggagagg cggtttgcgt attgggcgcc agggtggttt tcttttcac cagtgagacg    1740
ggcaacagct gattgccctt caccgcctgg ccctgagaga gttgcagcaa gcggtccacg    1800
ctggtttgcc ccagcaggcg aaaatcctgt ttgatggtgg ttaacggcgg gatataacat    1860
gagctgtctt cggtatcgtc gtatcccact accgagatgt ccgcaccaac gcgcagcccg    1920
gactcggtaa tggcgcgcat tgcgcccagc gccatctgat cgttggcaac cagcatcgca    1980
gtgggaacga tgccctcatt cagcatttgc atggtttgtt gaaaaccgga catggcactc    2040
cagtcgcctt cccgttccgc tatcggctga atttgattgc gagtgagata tttatgccag    2100
ccagccagac gcagacgcgc cgagacagaa cttaatgggc ccgctaacag cgcgatttgc    2160
tggtgaccca atgcgaccag atgctccacg cccagtcgcg taccgtcttc atgggagaaa    2220
```

```
ataatactgt tgatgggtgt ctggtcagag acatcaagaa ataacgccgg aacattagtg    2280
caggcagctt ccacagcaat ggcatcctgg tcatccagcg atagttaat gatcagccca     2340 ctgacgcgtt gcgcgagaag attgtgcacc gccgctttac aggcttcgac gccgcttcgt    2400
tctaccatcg acaccaccac gctggcaccc agttgatcgg cgcgagattt aatcgccgcg    2460
acaatttgcg acggcgcgtg cagggccaga ctggaggtgg caacgccaat cagcaacgac    2520
tgtttgcccg ccagttgttg tgccacgcgg ttgggaatgt aattcagctc cgccatcgcc    2580
gcttccactt tttcccgcgt tttcgcagaa acgtggctgg cctggttcac cacgcgggaa    2640
acggtctgat aagagacacc ggcatactct gcgacatcgt ataacgttac tggtttcaca    2700
ttcaccaccc tgaattgact ctcttccggg cgctatcatg ccataccgcg aaaggttttg    2760
cgccattcga tggtgtccgg gatctcgacg ctctccctta tgcgactcct gcattaggaa    2820
gcagcccagt agtaggttga ggccgttgag caccgccgcc gcaaggaatg tgtcgtcgc     2880 cgcacttatg actgtcttct ttatcatgca actcgtagga caggtgcctc aggtagcatc    2940
cgctaatctt atggataaaa atgctatggc atagcaaagt gtgacgccgt gcaaataatc    3000
aatgtggact tttctgccgt gattatagac acttttgtta cgcgttttg tcatggcttt     3060 ggtcccgctt tgttacagaa tgcttttaat aagcggggtt accggtttgg ttagcgagaa    3120
gagccagtaa aagacgcagt gacggcaatg tctgatgcaa tatggacaat tggtttcttc    3180
tctgaatggc gggagtatga aaagtatggc tgaagcgcaa aatgatcccc tgctgccggg    3240
atactcgttt aatgcccatc tggtggcggg tttaacgccg attgaggcca acggttatct    3300 cgatttttt atcgaccgac cgctgggaat gaaaggttat attctcaatc tcaccattcg     3360
cggtcagggg gtggtgaaaa atcagggacg agaatttgtt tgccgaccgg gtgatatttt    3420
gctgttcccg ccaggagaga ttcatcacta cggtcgtcat ccggaggctc gcgaatggta    3480
tcaccagtgg gtttactttc gtccgcgcgc ctactggcat gaatggctta actggccgtc    3540
aatatttgcc aatacggggt tctttcgccc ggatgaagcg caccagccgc atttcagcga    3600
cctgtttggg caaatcatta acgccgggca aggggaaggg cgctattcgg agctgctggc    3660
gataaatctg cttgagcaat tgttactgcg gcgcatggaa gcgattaacg agtcgctcca    3720
tccaccgatg gataatcggg tacgcgaggc ttgtcagtac atcagcgatc acctggcaga    3780
cagcaatttt gatatcgcca gcgtcgcaca gcatgtttgc ttgtcgccgt cgcgtctgtc    3840 acatctttc cgccagcagt tagggattag cgtcttaagc tggcgcgagg accaacgtat     3900
cagccaggcg aagctgcttt tgagcaccac ccggatgcct atcgccaccg tcggtcgcaa    3960
tgttggtttt gacgatcaac tctatttctc gcgggtattt aaaaaatgca ccggggccag    4020
cccgagcgag ttccgtgccg gttgtgaaga aaaagtgaat gatgtagccg tcaagttgtc    4080
ataattggta acgaatcaga caattgacgg gcagcgccca acagtccccc ggccacgggg    4140
cctgccacca tacccacgcc gaaacaagcg ccctgcacca ttatgttccg gatctgcatc    4200
gcaggatgct gctggctacc ctgtggaaca cctacatctg tattaacgaa gcgctaaccg    4260
tttttatcag gctctgggag gcagaataaa tgatcatatc gtcaattatt acctccacgg    4320
ggagagcctg agcaaactgg cctcaggcat ttgagaagca cacggtcaca ctgcttccgg    4380
tagtcaataa accggtaaac cagcaataga cataagcggc tatttaacga ccctgccctg    4440
aaccgacgac cgggtcgaat ttgctttcga atttctgcca ttcatccgct tattatcact    4500
tattcaggcg tagcaccagg cgtttaaggg caccaataac tgcctaaaaa aaattacgcc    4560
ccgccctgcc actcatcgca gtactgttgt aattcattaa gcattctgcc gacatggaag    4620
```

```
ccatcacaga cggcatgatg aacctgaatc gccagcggca tcagcaccct gtcgccttgc    4680
gtataatatt tgcccatggt gaaaacgggg gcgaagaagt tgtccatatt ggccacgttt    4740
aaatcaaaac tggtgaaact cacccaggga ttggctgaga cgaaaaacat attctcaata    4800 aacccttag ggaaataggc caggttttca ccgtaacacg ccacatcttg cgaatatatg    4860
tgtagaaact gccggaaatc gtcgtggtat tcactccaga gcgatgaaaa cgtttcagtt    4920
tgctcatgga aaacggtgta acaagggtga acactatccc atatcaccag ctcaccgtct    4980
ttcattgcca tacg                                                     4994
```

<210> SEQ ID NO 3
<211> LENGTH: 13
<212> TYPE: RNA
<213> ORGANISM: Artificial Sequence
<220> FEATURE:
<223> OTHER INFORMATION: Consensus Sequence of the Kozak sequence for
      mammals
<220> FEATURE:
<221> NAME/KEY: misc_feature
<222> LOCATION: (7)..(7)
<223> OTHER INFORMATION: n is a or g

<400> SEQUENCE: 3
gccgccncca ugg                                                      13

<210> SEQ ID NO 4
<211> LENGTH: 12
<212> TYPE: RNA
<213> ORGANISM: Artificial Sequence
<220> FEATURE:
<223> OTHER INFORMATION: Consensus sequence of the Kozak sequence of
      yeasts
<220> FEATURE:
<221> NAME/KEY: misc_feature
<222> LOCATION: (1)..(1)
<223> OTHER INFORMATION: n is a or u
<220> FEATURE:
<221> NAME/KEY: Intron
<222> LOCATION: (2)..(2)
<223> OTHER INFORMATION: test
<220> FEATURE:
<221> NAME/KEY: misc_feature
<222> LOCATION: (3)..(3)
<223> OTHER INFORMATION: n is a or c
<220> FEATURE:
<221> NAME/KEY: misc_feature
<222> LOCATION: (6)..(6)
<223> OTHER INFORMATION: n is a or c
<220> FEATURE:
<221> NAME/KEY: misc_feature
<222> LOCATION: (12)..(12)
<223> OTHER INFORMATION: n is u or c

<400> SEQUENCE: 4
nanaanaugu cn                                                       12

<210> SEQ ID NO 5
<211> LENGTH: 10
<212> TYPE: DNA
<213> ORGANISM: Artificial Sequence
<220> FEATURE:

```
<223> OTHER INFORMATION: sequence between recognition sequences
<220> FEATURE:
<221> NAME/KEY: misc_feature
<222> LOCATION: (4)..(7)
<223> OTHER INFORMATION: n is a, t, c or g

<400> SEQUENCE: 5 cacnnnngtg                                                              10
```